(12) United States Patent
Mostafavi

(10) Patent No.: US 7,711,087 B2
(45) Date of Patent: May 4, 2010

(54) PATIENT SETUP USING TOMOSYNTHESIS TECHNIQUES

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 395 days.

(21) Appl. No.: 11/400,760

(22) Filed: Apr. 7, 2006

(65) Prior Publication Data

US 2007/0237290 A1 Oct. 11, 2007

(51) Int. Cl.
*A61N 5/10* (2006.01)

(52) U.S. Cl. ............................... 378/65; 378/4; 378/22; 382/294

(58) Field of Classification Search .................... 378/4, 378/21–25, 65; 382/294
See application file for complete search history.

(56) References Cited

U.S. PATENT DOCUMENTS

| 7,245,698 | B2 | 7/2007 | Pang et al. | |
|---|---|---|---|---|
| 7,453,976 | B1 | 11/2008 | Yin | |
| 2003/0007601 | A1* | 1/2003 | Jaffray et al. | 378/65 |
| 2005/0059887 | A1* | 3/2005 | Mostafavi et al. | 600/427 |
| 2005/0117708 | A1* | 6/2005 | Cho et al. | 378/164 |
| 2006/0098855 | A1* | 5/2006 | Gkanatsios et al. | 382/128 |
| 2007/0025509 | A1* | 2/2007 | Pang et al. | 378/65 |
| 2007/0189591 | A1* | 8/2007 | Lu et al. | 382/128 |

OTHER PUBLICATIONS

Badea, Volume Imaging Using a Combined Cone Beam CT-DTS Approach, 2000, Doctorate Thesis, University of Patras.*
Baydush et al., Initial application of digital tomosynthesis with on-board imaging in radiation oncology, Feb. 13, 2005, Medical Imaging 2005: Physics of Medical Imaging, SPIE vol. 5745, p. 1300-1305.*
Li et al., The impact of acquisition angular range on the z-resolution of radiographic tomosynthesis, Jun. 2004, International Congress Series, vol. 1268, pp. 13-18, Proceedings of the 18th International Congress and Exposition—CARS 2004—Computer Assisted Radiography and Surgery.*

(Continued)

*Primary Examiner*—Allen C. Ho
*Assistant Examiner*—John M Corbett
(74) *Attorney, Agent, or Firm*—Vista IP Law Group, LLP

(57) ABSTRACT

A system for determining a position of an object includes an imaging system having a x-ray source and an imager, and a processor configured to obtain a tomosynthesis image of an object using the imaging system, and determine a position of the object using the tomosynthesis image. A method of determining a position of an object includes obtaining a tomosynthesis image of an object, and determining a coordinate of the object relative to a radiation machine using the tomosynthesis image. A device for determining a position of an object includes a processor for determining a coordinate of the object relative to a radiation machine using a tomosynthesis image. A method of determining a position of an object includes obtaining an image of an object, obtaining a reference image of the object, comparing the reference image with the image, and determining a coordinate of the object based at least in part on a result of the comparing, wherein the reference image has a plane that is parallel with a plane of the image.

39 Claims, 13 Drawing Sheets

OTHER PUBLICATIONS

Pang et al., Just-in-time tomography (JiTT): a new concept for image-guided radiation therapy, Oct. 20, 2005, Phys. Med. Biol., 50, N323-N330.*

Godfrey et al., Digital Tomosynthesis for Verification of Radiation Therapy Positioning: Preliminary Results from a Kilovoltage On-Board Imaging System, Abstract No. SU-FF-J-57, Medical Physics, vol. 32, No. 6, Jun. 2005.*

Godfrey et al., Online Digital Tomosynthesis (DTS): A Novel Technique for Improving Target Localization in Radiation Therapy, Sep. 21, 2005, International Journal of Radiation Oncology Biology Physics Abstract Final ID: 2542, vol. 63, Supplement 1, p. S556.*

Oldham et al., Cone-beam-CT guided radiation therapy: A model for on-line application, May 10, 2005, Radiotherapy and Oncology, vol. 75, pp. 271.e1-271.e8.*

Godfrey et al., Digital Tomosynthesis for Verification of Radiation Therapy Positioning: Preliminary Results From a Kilovoltage On-Board Imaging System, Jun. 2005, Medical Physics, vol. 32, No. 6, p. 1932.*

Oldham et al., On-Line Volumetric CT-Guided Radiation Therapy, 2003, International Journal of Radiation Oncology, vol. 57, No. 2, Supplement, Abstract No. 101, p. S184.*

Godfrey et al., Practical Strategies for the clinical implementation of matrix inversion tomosynthesis (MITS), 2003, Proceedings of the SPIE, vol. 5030, pp. 379-390.*

Godfrey et al., Online Digital Tomosynthesis (DTS): A Novel Technique for improving Target Localization in Radiation Therapy, available online Sep. 21, 2005, International Journal of Radiation Oncology in Biology and Physics, Final Abstract Id 2542, vol. 63, Supplement 1, p. S556.*

* cited by examiner

Equations $$v(x, y, z) = \sum_i p_i(u_i, v_i) \tag{1}$$

$$u_i = d_u \cdot f \cdot x / (d - z \cos \alpha_i + y \sin \alpha_i) \tag{2}$$

$$v_i = d_v \cdot f \cdot (y \cos \alpha_i + z \sin \alpha_i) / (d - z \cos \alpha_i + y \sin \alpha_i) \tag{3}$$

==================

$$v_b(x, y, z_k) = \frac{1}{N_c} \sum_{\substack{j \\ j \neq k}} \sum_i v(x_i, y_i, z_j) \tag{4}$$

$$V_{deblurred}(x, y, z_k) = v(x, y, z_k) - v_b(x, y, z_k) \tag{5}$$

$$x_i = x(d \cos \alpha_i - z_j) / (d \cos \alpha_i - z_k) \tag{6}$$

$$y_i = (y - d \sin \alpha_i)(d \cos \alpha_i - z_j) / (d \cos \alpha_i - z_k) \tag{7}$$

FIG. 5B

PATIENT SETUP USING TOMOSYNTHESIS TECHNIQUES

BACKGROUND

1. Field

This application relates generally to radiation devices, and more specifically, to treatment and diagnostic radiation devices that generate and/or use tomosynthesis images.

2. Background

Various systems and methods exist to provide radiation therapy treatment of tissue (e.g., tumorous tissue) with high-energy radiation. While some patient conditions require whole body radiation treatments, many forms of radiation treatment benefit from the ability to accurately control the amount, location and distribution of radiation within a patient's body. Such control often includes using a multi-leaf collimator to shape a radiation beam such that the beam has a shape that approximates that of the tumorous region.

Regardless of the form of radiation, many existing radiation treatment procedures require a location of a target region be determined in order to accurately register the target region relative to a radiation source before radiation is applied to the target region. This requires a 3D image of the tumor and surrounding tissue, and is generally accomplished by performing a computed tomography. Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking thousands of readings from multiple angles around the patient, relatively massive amounts of data are thus accumulated. The accumulated data are then analyzed and processed for reconstruction of a matrix (visual or otherwise), which constitutes a depiction of a density function of the bodily section being examined.

A problem associated with registering a target tissue using a CT image is that the CT image may take too long to obtain. In order to perform CT image reconstruction, a sufficient amount of CT image data needs to be generated over a prescribed range of gantry angles. These CT image data take time to generate. Mechanical configuration and/or regulatory rules may limit the rotation rate of a gantry on which the x-ray source and the image detector are mounted. The CT imaging devices that are attached to the gantry of radiation therapy machines have rotation speed that is limited to one rotation per minute. Because of the duration required to generate sufficient CT image data, a patient may not feel comfortable confined within a gantry opening.

In some cases, it may be desirable to continuously monitor a position of a target tissue while a treatment procedure is being performed. For example, a target tissue may move due to physiological movement (e.g., breathing, cardiac motion, coughing, etc.) of a patient. In such cases, it would be desirable to track a movement of the target tissue to ensure that a treatment radiation beam is accurately aimed towards the target tissue. In existing radiation treatment systems, tracking of target tissue does not use CT imaging technique. This is because collecting a sufficient quantity of CT image data for image reconstruction while considering breathing motion may take a long time, and therefore, may not be performed at a fast enough rate, at least not fast enough for real-time tracking of target tissue.

SUMMARY

In accordance with some embodiments, a system for determining a position of an object includes an imaging system having a x-ray source and an imager, and a processor configured to obtain a tomosynthesis image of an object using the imaging system, and determine a position of the object using the tomosynthesis image.

In accordance with other embodiments, a method of determining a position of an object includes obtaining an image of an object, obtaining a reference image of the object, comparing the reference image with the image, and determining a coordinate of the object based at least in part on a result of the comparing, wherein the reference image has a plane that is parallel with a plane of the image.

In accordance with other embodiments, a device for setting up an object in a radiation procedure includes a processor configured for obtaining an image of an object, obtaining a reference image of the object, comparing the reference image with the image, and determining a coordinate of the object based at least in part on a result of the comparing, wherein the reference image has a plane that is parallel with a plane of the image.

In accordance with other embodiments, a method of determining a position of an object includes obtaining a tomosynthesis image of an object, and determining a coordinate of the object relative to a radiation machine using the tomosynthesis image.

In accordance with other embodiments, a device for determining a position of an object includes a processor for determining a coordinate of the object relative to a radiation machine using a tomosynthesis image.

In accordance with other embodiments, a method of determining a position of an object includes obtaining a first tomosynthesis image of an object, determining a first two dimensional coordinate of the object using the first tomosynthesis image, obtaining a second tomosynthesis image of the object, determining a second two dimensional coordinate of the object using the second tomosynthesis image, and determining a three dimensional coordinate of the object based on the first and the second two dimensional coordinates. In some embodiments, position in a third dimension (e.g., depth) is also obtained.

In accordance with other embodiments, a device for determining a position of an object includes a processor configured for obtaining a first tomosynthesis image of an object, determining a first two dimensional coordinate of the object using the first tomosynthesis image, obtaining a second tomosynthesis image of the object, determining a second two dimensional coordinate of the object using the second tomosynthesis image, and determining a three dimensional coordinate of the object based on the first and the second two dimensional coordinates.

In accordance with other embodiments, a method of determining a position of an object includes obtaining an image of an object, and determining a coordinate of the object relative to a radiation machine using the image, wherein the image is obtained by receiving a plurality of x-ray images and processing the x-ray images using a back projection technique.

Other aspects and features will be evident from reading the following detailed description of the embodiments.

BRIEF DESCRIPTION OF THE DRAWINGS

The drawings illustrate the design and utility of embodiments, in which similar elements are referred to by common reference numerals. In order to better appreciate how advantages and objects of the embodiments are obtained, a more particular description of the embodiments will be illustrated in the accompanying drawings.

FIG. 5B illustrates equations that can be used to construct tomosynthesis image in accordance with some embodiments;

DETAILED DESCRIPTION OF THE EMBODIMENTS

Figure 1:
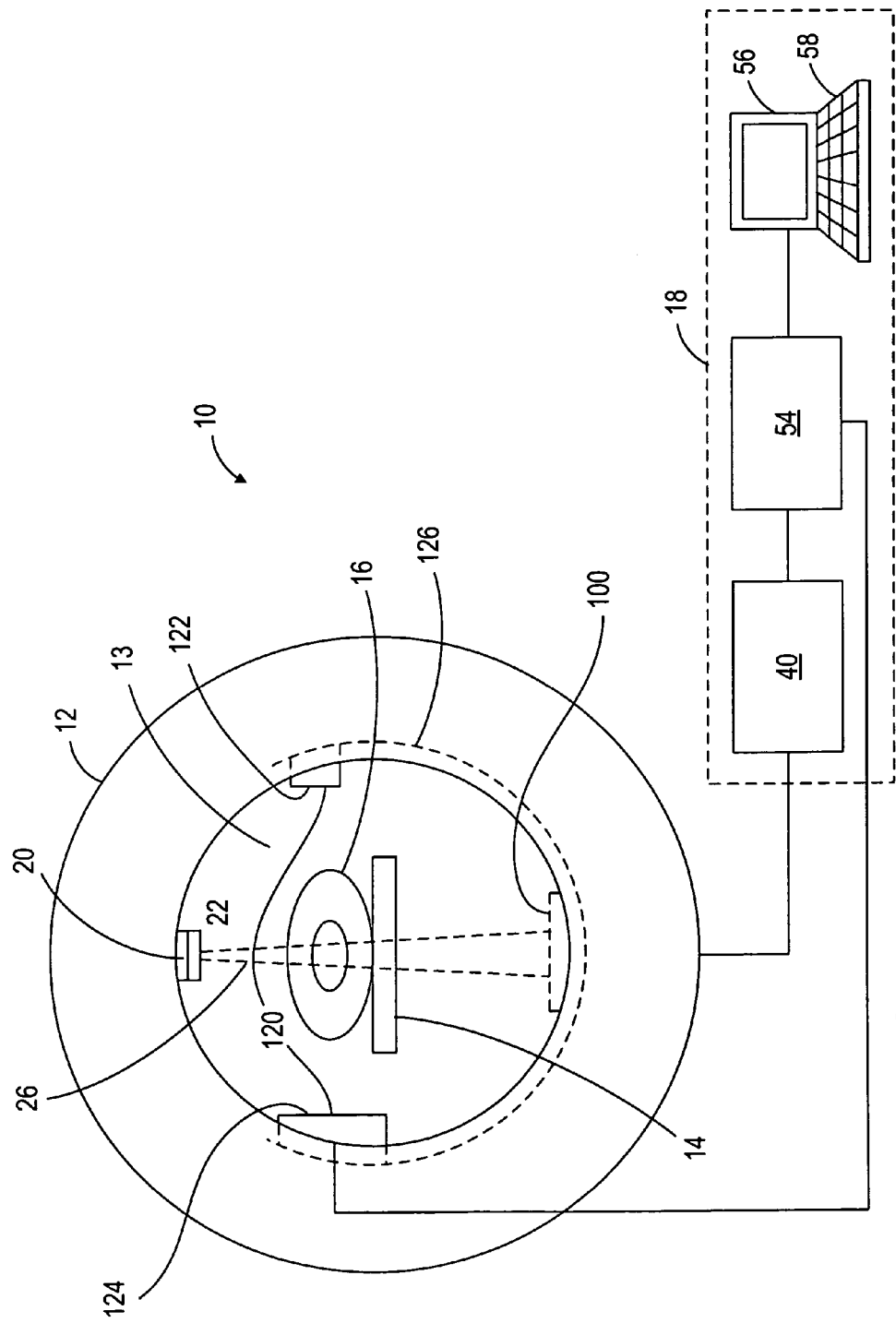
FIG. 1 illustrates a radiation treatment system having a tomosynthesis imaging system in accordance with some embodiments.

Various embodiments are described hereinafter with reference to the figures. It should be noted that the figures are not drawn to scale and elements of similar structures or functions are represented by like reference numerals throughout the figures. It should also be noted that the figures are only intended to facilitate the description of embodiments. They are not intended as an exhaustive description of the invention or as a limitation on the scope of the invention. In addition, an aspect described in conjunction with a particular embodiment is not necessarily limited to that embodiment and can be practiced in any other embodiments.

FIG. 1 illustrates a radiation treatment system 10 in accordance with some embodiments. The system 10 includes a gantry 12 having an opening (or bore) 13, a patient support 14 for supporting a patient 16, and a control system 18 for controlling an operation of the gantry 12. The system 10 also includes a radiation source 20 that projects a beam 26 of radiation towards the patient 16 while the patient 16 is positioned at least partially within the opening 13, and a collimator system 22 for controlling a delivery of the radiation beam 26. The radiation source 20 can be configured to generate a cone beam, a fan beam, or other types of radiation beams in different embodiments.

In the illustrated embodiments, the radiation source 20 is a treatment radiation source for providing treatment energy. In other embodiments, in addition to being a treatment radiation source, the radiation source 20 can also be a diagnostic radiation source for providing diagnostic energy. In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 20 is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source 20 can be a diagnostic radiation source.

In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). In other embodiments, the gantry 12 does not rotate about the patient 16 during a treatment procedure, and the position of the radiation source 20 remains fixed relative to the patient support 14. The operation of the radiation source 20, the collimator system 22, and the gantry 12 (if the gantry 12 is rotatable), are controlled by the control 40, which provides power and timing signals to the radiation source 20 and the collimator system 22, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

In some embodiments, the system 10 can further include an imager 100 (shown in dotted-line in the figure) located next to the opening 13 and opposite from the radiation source 20. Such configuration allows the patient 16 to be imaged and treated without removing the patient 16 from the system 10. In some embodiments, the imager 100 includes a conversion layer made from a scintillator element, such as Cesium Iodide (CsI), and a photo detector array (e.g., a photodiode layer) coupled to the conversion layer. The conversion layer generates light photons in response to radiation, and the photo detector array, which includes a plurality of detector elements, is configured to generate electrical signal in response to the light photons from the conversion layer. The imager 100 can have a curvilinear surface (e.g., a partial circular arc). Such configuration is beneficial in that each of the imaging elements of the imager 100 is located substantially the same distance from the radiation source 20. In an alternative embodiment, the imager 100 may have a rectilinear surface or a surface having other profiles. The imager 100 can be made from amorphous silicon, crystal and silicon wafers, crystal and silicon substrate, or flexible substrate (e.g., plastic), and may be constructed using flat panel technologies or other techniques known in the art of making imaging device. In alternative embodiments, the imager 100 may use different detection schemes. For example, in alternative embodiments, instead of having the conversion layer, the imager 100 may include a photoconductor, which generates electron-hole-pairs or charges in response to radiation.

During a diagnostic procedure, the radiation source 20 generates and directs a radiation beam towards the patient 16, while the detector 100 measures the radiation absorption at a plurality of transmission paths defined by the radiation beam during the process. The detector 100 produces a voltage proportional to the intensity of incident radiation, and the voltage is read and digitized for subsequent processing in a computer, such as the processor 54 or another processor. After image data at different gantry angles have been collected, the collected data are processed for reconstruction of a matrix (CT image), which constitutes a depiction of a density function of the bodily section being examined. By considering one or more of such sections, a skilled diagnostician can often diagnose various bodily ailments. In some cases, the one or more sections can also be used to perform treatment planning, and/or to verify a position of a target tissue.

It should be noted that the radiation treatment system 10 should not be limited to the configuration described previously, and that the radiation treatment system 10 can also have other configurations in other embodiments. For example, in other embodiments, instead of a ring-configuration, the radiation treatment system 10 can have a C-arm configuration. Also, in other embodiments, the radiation system 10 can include an arm to which the radiation source 20 is secured. In further embodiments, the radiation system 10 can have configurations that are known in the art of radiation systems.

Returning to FIG. 1, the treatment system 10 further includes an imaging system 120 having a x-ray source 122 and an imager 124. In the illustrated embodiments, the x-ray source 122 and the imager 124 are mounted to a ring 126 next to the gantry 12, wherein the ring 126 can be rotated to change a position of the imager 124 relative to a patient. The ring 126 is also moveable independent of the gantry 12, thereby allowing the x-ray source 122 to move relative to the radiation source 20. In other embodiments, the x-ray source 122 and the imager 124 can be mounted on other structures, such as a C-arm, a mechanical linkage, or a component of the treatment system 10. During use, the x-ray source 122 emits radiation towards an object, such as a patient, and the imager 124 measures the radiation absorption at a plurality of transmission paths defined by the radiation. The imager 124 produces a voltage proportional to the intensity of incident radiation, and the voltage is read and digitized for subsequent processing in a computer, such as the processor 54, or another processor. In some embodiments, the imaging system 120 also includes a processor, such as the processor 54, for processing image data generated by the imager 124.

Figure 2:
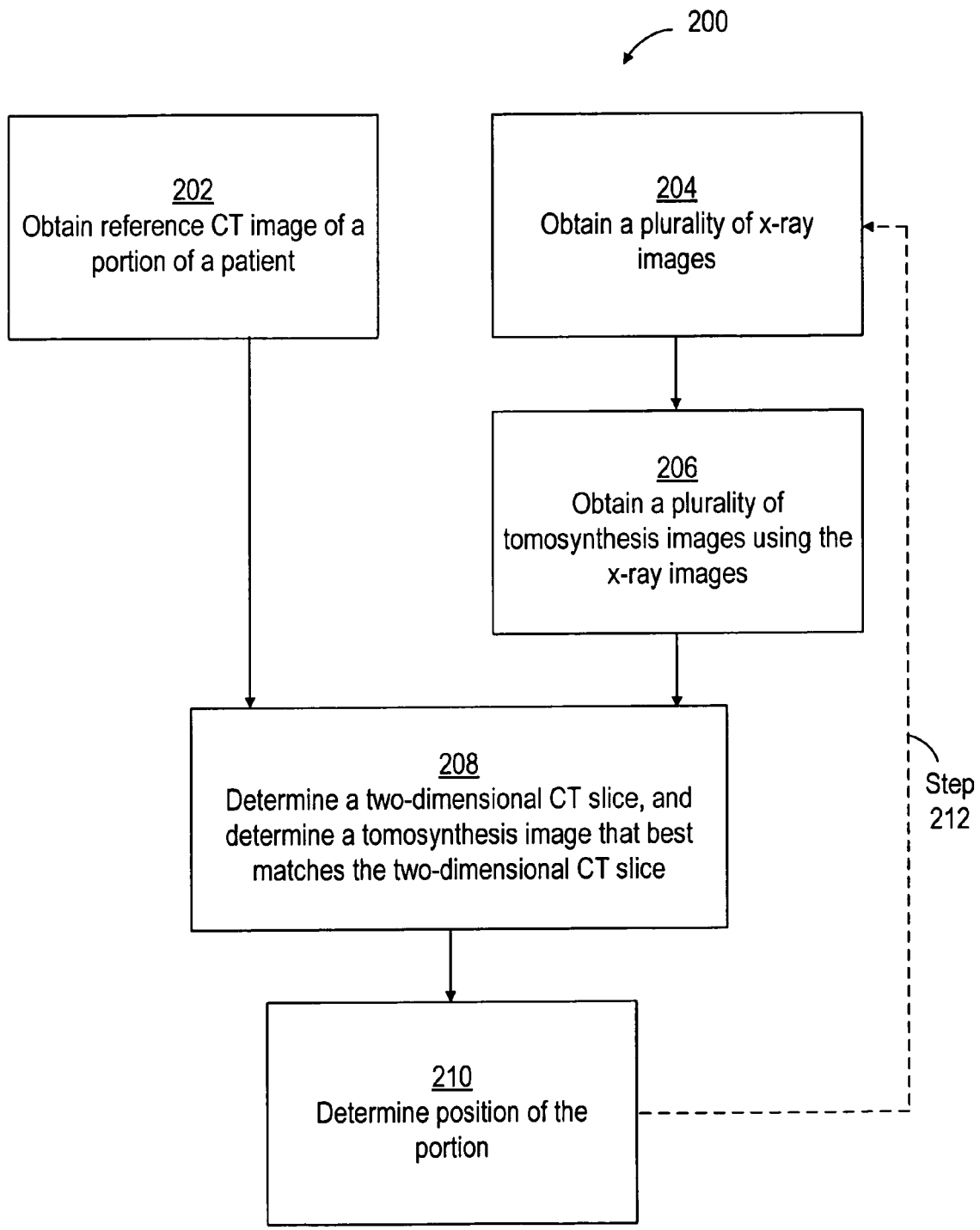
FIG. 2 illustrates a method of determining a position of at least a portion of a target tissue using the tomosynthesis imaging system of FIG. 1 in accordance with some embodiments.

A method 200 of using the imaging system 120 to perform patient registration for the treatment system 10 in accordance with some embodiments will now be described with reference to FIG. 2. First, a computed tomography (CT) image is obtained for a portion of the patient 16 (Step 202). Such can be performed, for example, in a diagnostic session in which the patient 16 is diagnosed, or in a treatment planning session in which a treatment plan is determined. In some embodiments, the CT image can be obtained by using a CT machine to deliver diagnostic radiation energy towards the patient 16. In other embodiments, if the radiation source 20 is configured to deliver diagnostic energy, and the system 10 includes the imager 100, the system 10 itself can be used to obtain the CT image. In such cases, the patient 16 is placed on the patient support 14, and a computed tomography procedure is performed to obtain a three-dimensional image of a portion (e.g., a target region) of the patient 16. In the computed tomography procedure, the radiation source 20 and the detector 100 are used to create a plurality of image data at different gantry angles (e.g., by rotating the gantry 12), which are then processed to reconstruct the three-dimensional CT image. CT procedure is known in the art of imaging, and will not be described in detail. In other embodiments, instead of using diagnostic radiation energy to create the plurality of image data, if the radiation source 20 is capable of delivering treatment radiation energy, such can be used to obtain the image data. For example, images obtained from a MeV source, such as, a series of low-dose images obtained using an electronic portal imaging device (EPID), can be used. In some embodiments, the EPID includes an MeV imager that produces image(s). It can be used to do low-dose imaging for patient positioning prior to delivering a treatment dose. In low-dose imaging, each image is produced with a much smaller number of energy pulses than that associated with a treatment dose. In further embodiments, the step 202 of obtaining a CT image can be performed by retrieving stored image data from a storage device or medium, such as that associated with a server or a computer.

Figure 3:
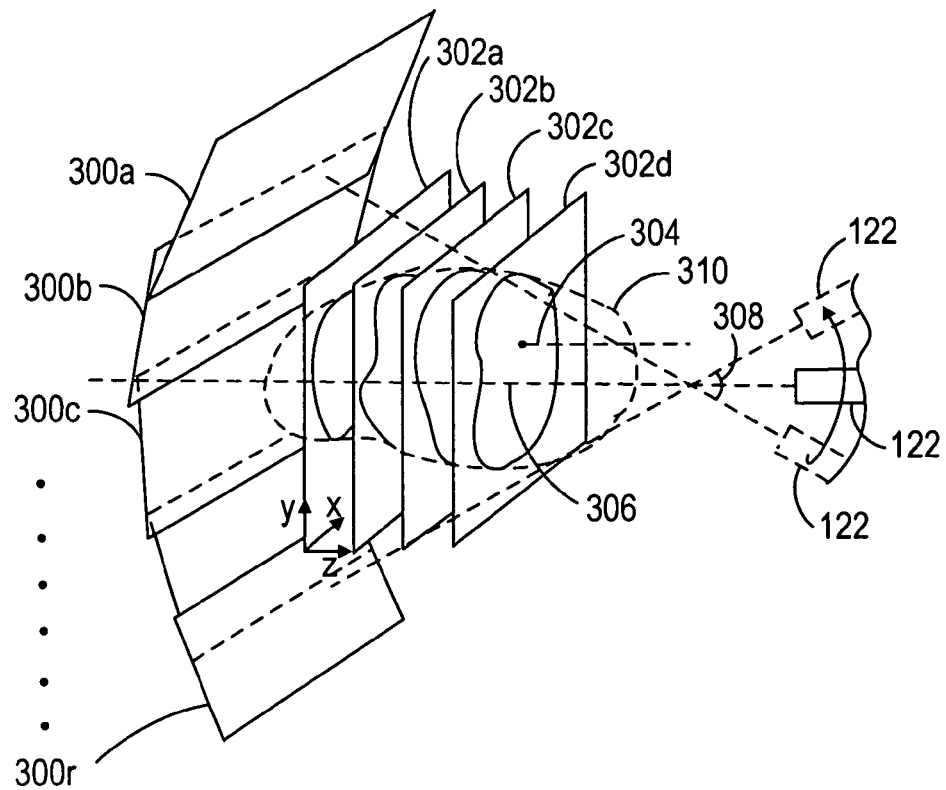
FIG. 3 illustrates a plurality of tomosynthesis images generated using the tomosynthesis imaging system of FIG. 1.

Next, during a treatment session, the patient 16 is placed in an operative position associated with the treatment system 10, and the imaging system 120 is used to generate a set of two-dimensional x-ray images (Step 204). As shown in FIG. 3, in some embodiments, the x-ray images 300 are generated by rotating the x-ray source 122 and the imager 124 about at least a portion of the patient 16, and activating the x-ray source 122 to deliver diagnostic radiation when the x-ray source 122 is at certain prescribed positions (e.g., rotational angles). In the illustrated embodiments, the x-ray source 122 rotates through a range 308 of 10° arch to generate eighteen x-ray images 300a-300r of at least a portion of a target tissue 310. In other embodiments, the x-ray source 122 can be configured to rotate through a different rotational range 308 (e.g., an angle larger than 10°), and/or the number of x-ray images 300 generated can be different from eighteen (e.g., more or less than eighteen). In other embodiments, the angle range 308 can be a value that is between 5° and 35°. Also, in other embodiments, the number of x-ray images 300 can be a value that is between 2 and 40. In the illustrated embodiments, the x-ray images 300 are in digitized form. In other embodiments, the x-ray images 300 can be generated with different geometries. For example, the relative position between the x-ray source 122 and imager 124 can be different from that described. Also, in other embodiments, there can be gaps in the angular range 308 over which the images 300 are acquired. In further embodiments, the angular spacing between the images 300 can be non-uniform.

Next, the processor 54 processes the x-ray images 300 to generate a plurality of tomosynthesis images 302 (Step 206). As shown in FIG. 3, each tomosynthesis image 302 has an axis 304 perpendicular to the imaging plane, wherein the axis 304 is approximately parallel to a bisector 306 of the rotational angle 308. In other embodiments, the tomosynthesis images 302 can have different orientations. For example, in some cases, the tomosynthesis images 302 are not on planar surfaces (e.g., they may be constructed on curvilinear surfaces). Also, in other embodiments, the axis 304 is not approximately parallel to, and forms an angle with, the bisector 306. In the illustrated embodiments, four tomosynthesis images 302a-302d are shown from a generated set that can include any number of images, such as up to 80 images, or up to 20 images, with a spacing between adjacent image 302 that is between 2 millimeter (mm) and 15 mm (e.g., 7 mm). In general, the spacing and the number of images 302 can be anything, and can be selected based on 1) depth (in the z-axis direction) resolution, and/or 2) the range of depth desired to be covered by the tomosynthesis images 302. In other embodiments, more or less tomosynthesis images 302 may be generated. For example, in other embodiments, the processor 54 generates one tomosynthesis image. Also, in further embodiments, the geometric spacing between the tomosynthesis images 302 may be different from that discussed previously.

In a tomosynthesis imaging procedure, each of the tomosynthesis images 302 is constructed by determining a plurality of voxels, wherein each voxel is determined by considering evidence of attenuation (e.g., an image or a characteristic) of that voxel in the input images 300. This evidence is accumulated from all input images 300 to estimate the attenuation of the voxel. The attenuation of the voxel is partly represented by the value of its corresponding pixel in each input image 300. The pixel value also includes attenuation from all other voxels in the ray that projects from the x-ray source 122 through the voxel and to the image 300. By adding the value of pixels from all images 300 that correspond to the voxel, the effect of attenuation at that voxel is constructively accumulated. The calculation of the pixel position and value for each voxel is based on x-ray photogrammetry and known geometry of the image detector 124 and x-ray source 122 for each acquired input image 300. Such technique is called "back projection."

As used in this specification, the term "tomosynthesis image" or "tomosynthesis slice" refers to an image created using a number of projection images in a back projection technique, wherein the number of projection images (input images) is less than that in a set that is required for a CT image reconstruction, and/or the trajectory of source and detector is less restricted than that used in a CT imaging procedure. For the purpose of this definition, the term "projection image" covers both emission projection images as well as x-ray transmission projection images. Also, in some embodiments, for the purpose of this definition, a set of images that is required for CT image reconstruction is considered to include images (e.g., 300 or more) generated over a range of gantry rotation that is 180° plus the fan beam angle. In some embodiments, the projection images for constructing a tomosynthesis image are taken over an angular range, which is a value between 1° and an angular range value X that is less than that needed for a complete projection set for CT imaging (e.g., with X being 180° plus the fan angle), wherein the number of projection images generated in this range is a value that is between 1-1000 (e.g., 2). In other embodiments, the projection images for constructing a tomosynthesis image are taken over an angular range, which is a value between 5° and 45°, wherein the number of projection images generated in this range is a value that is between 5-100.

Figure 5A:
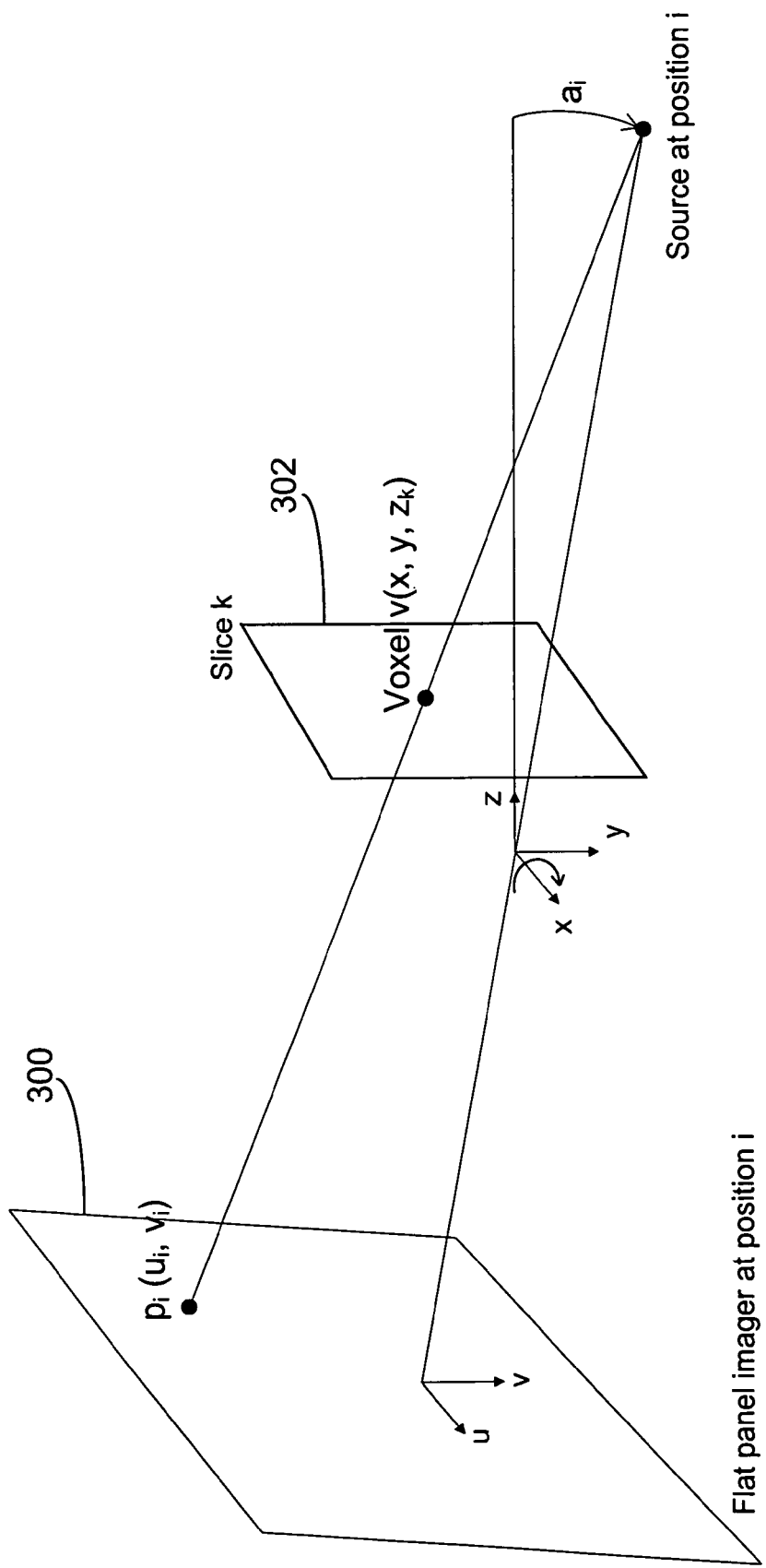
FIG. 5A is a diagram illustrating principles of constructing a tomosynthesis image in accordance with some embodiments.

An example of a technique for constructing tomosynthesis image(s) in accordance with some embodiments will now be described with reference to FIGS. 5A and 5B. In general, the process of back projection can be defined by Equation 1 of FIG. 5B. This equation applies to all source-imager movement geometries and not just the isocentric movement geometry associated with the system 10 of FIG. 1. The voxel value $V(x, y, z)$ in a tomosynthesis image 302 at location (x, y, z) in space is the sum of the pixel values $P_i(u_i, v_i)$ from input images 300 where $(u_i, v_i)$ is the pixel coordinates of the projection of the voxel V(x, y, z) onto the image $P_i$. In the illustrated example, the x-ray source 122 and imager 124 form a rigid body that is defined by the fixed source-imager distance, f, and the fixed principal point, which is the base of the principal axis (i.e. the normal dropped from the source to the imager plane). The principal point is defined as the origin (0, 0) of the pixel coordinates (u, v) for each image. For the isocentric movement scenario, the source-imager rigid body rotates around a fixed center of rotation without any precession. In some cases, the requirement that the u axis of the pixel grid on the imager plane remain parallel to the rotation axis (i.e., no roll of the imager 124 about the principal axis) is imposed. This allows the origin of the three-dimensional reconstruction coordinates (x, y, z) to be defined at the center of rotation, with the x axis aligned with the fixed rotation axis. The source 122 traverses a circular arc segment in the y-z plane where the radius of the circle is the fixed source-axis distance, d. The finite number of input images 300 acquired over this arc segment defines its beginning and end points. For any set of input images 300, the z axis is defined such that it points towards the center of the arc segment. Each image $P_i$ corresponds to a rotation angle $a_i$ between the principal axis and the z axis as defined above and shown in FIG. 5A, which shows a reconstructed slice 302 and the source-imager position for one of the input images 300. For the isocentric geometry scenario, Equations 2 and 3 of FIG. 5B give the pixel coordinates $(u_i, v_i)$ of the projection of the voxel V(x, y, z) in each image $P_i$. The pixel pitch on the imager plane is denoted by du and $d_v$ in the u and v directions, respectively.

Using Equations 1-3 of FIG. 5B, one can determine an estimate of the attenuation for any voxel. A tomosynthesis slice is a contiguous arrangement of voxels in the three-dimensional space that forms a surface. For the isocentric geometry scenario, the tomosynthesis slice may be defined as a planar and rectilinear arrangement of voxels, where as shown in FIG. 5A, the plane is normal to the z axis, and the grid is aligned with the x and y axes. A collection of parallel tomosynthesis slices form a three-dimensional rectilinear grid of voxels, whose relative values can each be estimated as described above. The voxel spacing in x, y and z and the number of slices are input parameters to the tomosynthesis construction process. On the other hand, the voxel size or resolution depends on the number and geometry of the input images 300. The voxel size in x and y-directions are limited by the imager native pixel pitch projected to the voxel position, which for this geometry, can be smaller than the imager pixel pitch. The voxel resolution in z or depth direction is at least partially governed by the angular coverage 308 or the length of the arc segment over which the input images 300 are acquired.

Because the attenuations of other voxels are also added but not in a non-constructive fashion, blurring of the reconstructed tomosynthesis image(s) 302 may result. Various methods can be performed to address this blurring. In some embodiments, the tomosynthesis image(s) 302 can be deblurred by performing back projection combined with filtering. The filtering can be done before back projection (filtered back projection method), or after back projection. De-blurred tomosynthesis images generated based on filtered back projection can be adopted from traditional computed tomography, and are based on inverse of Radon transform using the back-projection theorem. However unlike computed tomography, the set of input images 300 for the tomosynthesis image(s) may not be a complete data set (relative to that required for reconstructing a CT image).

In accordance with other embodiments, a three dimensional deblurring filter can be applied after back projection. In such cases, a prescribed number of tomosynthesis images (or slices) that cover the volume of interest are first constructed. Then the three-dimensional deblurring filter is applied to these tomosynthesis slices. In one filtering technique, the knowledge of the imaging geometry is used to model the blur caused in each tomosynthesis slice due to contrast features in all other tomosynthesis slices in the constructed set. This process forms a "blur slice" specifically for the slice being deblurred and is subtracted from it. This is repeated for all tomosynthesis slices in the reconstructed set. This whole process can be repeated in iterative fashion to further remove the blur caused by out-of-slice contrast features from each tomosynthesis slice.

Figure 5C:
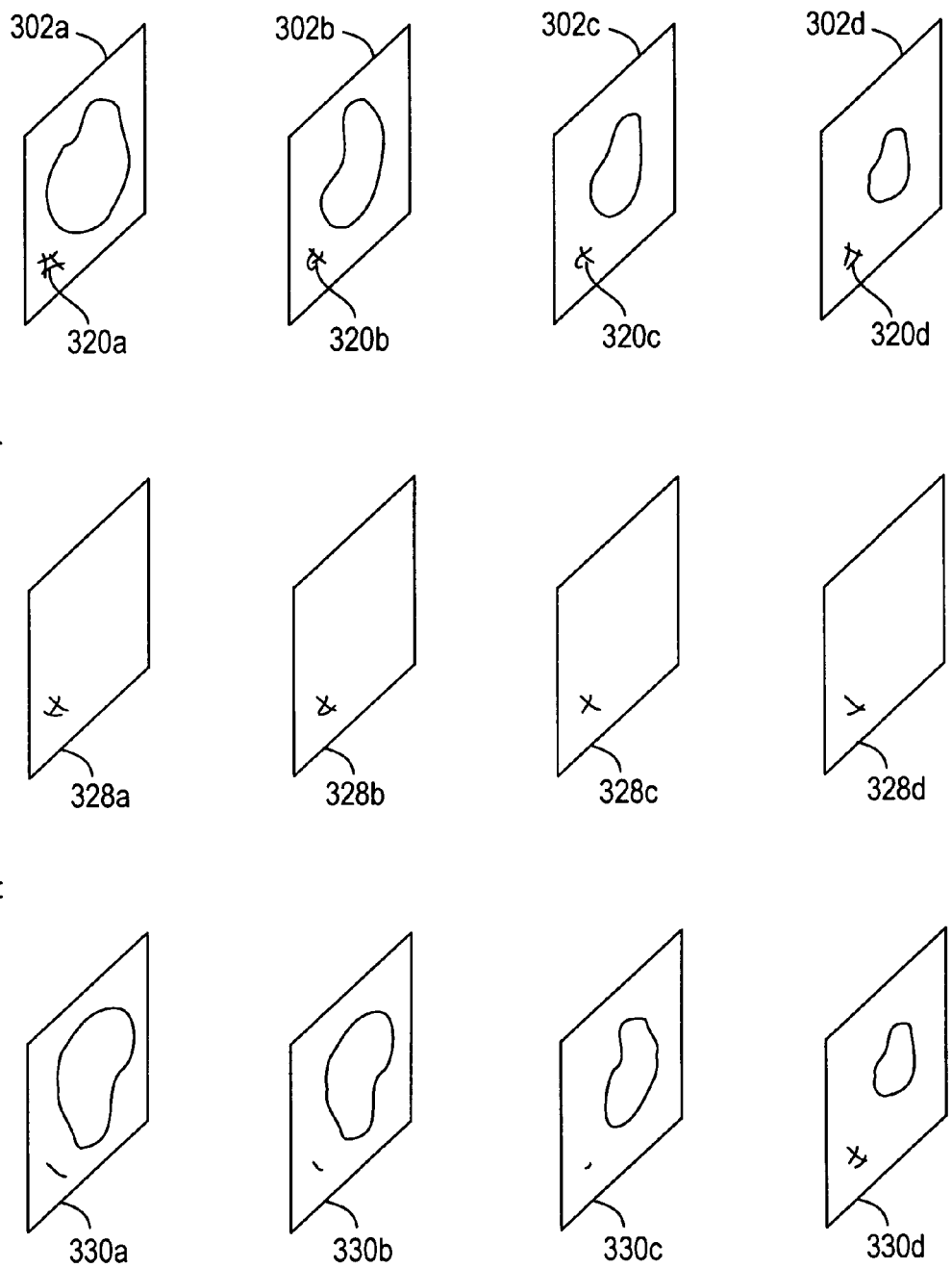
FIGS. 5C and 5D illustrate an example of a technique used to enhance tomosynthesis images.

To illustrate, refer to FIG. 5C, which shows that a blurry image 320a in the tomosynthesis image 302a can be removed, or at least reduced, by determining a correction image (blur slice) 328a using the images 320b-320d, and subtracting the correction image 328a from the tomosynthesis image 320a to thereby obtain an enhanced (or modified) tomosynthesis image 330a. Similarly, the same technique can be performed on the tomosynthesis image 302b using the blurry images 320a, and 320c-320d, to thereby create an enhanced tomosynthesis image 330b. Also, the same technique can be performed on the tomosynthesis image 302c using the blurry image 320a-320b, and 320d, to thereby create an enhanced tomosynthesis image 330c. The same technique can also be performed on the tomosynthesis image 302d using the blurry image 320a-320c, to thereby create an enhanced tomosynthesis image 330d. As shown in the illustrated embodiments, the correction image is calculated from all (or a subset of all) tomosynthesized images except the one being corrected. The above procedure can be performed once (in a first iteration) to generate a set of enhanced tomosynthesis images. If desired, the same procedure can be performed again (e.g., in a second or third iteration), this time using the set of enhanced tomosynthesis images, until tomosynthesis images having desired characteristics are obtained. In other embodiments, the deblurring procedure is not performed. This has the benefits of reducing computation time for the processor 54, and improving the efficiency of the method 200.

Figure 5D:
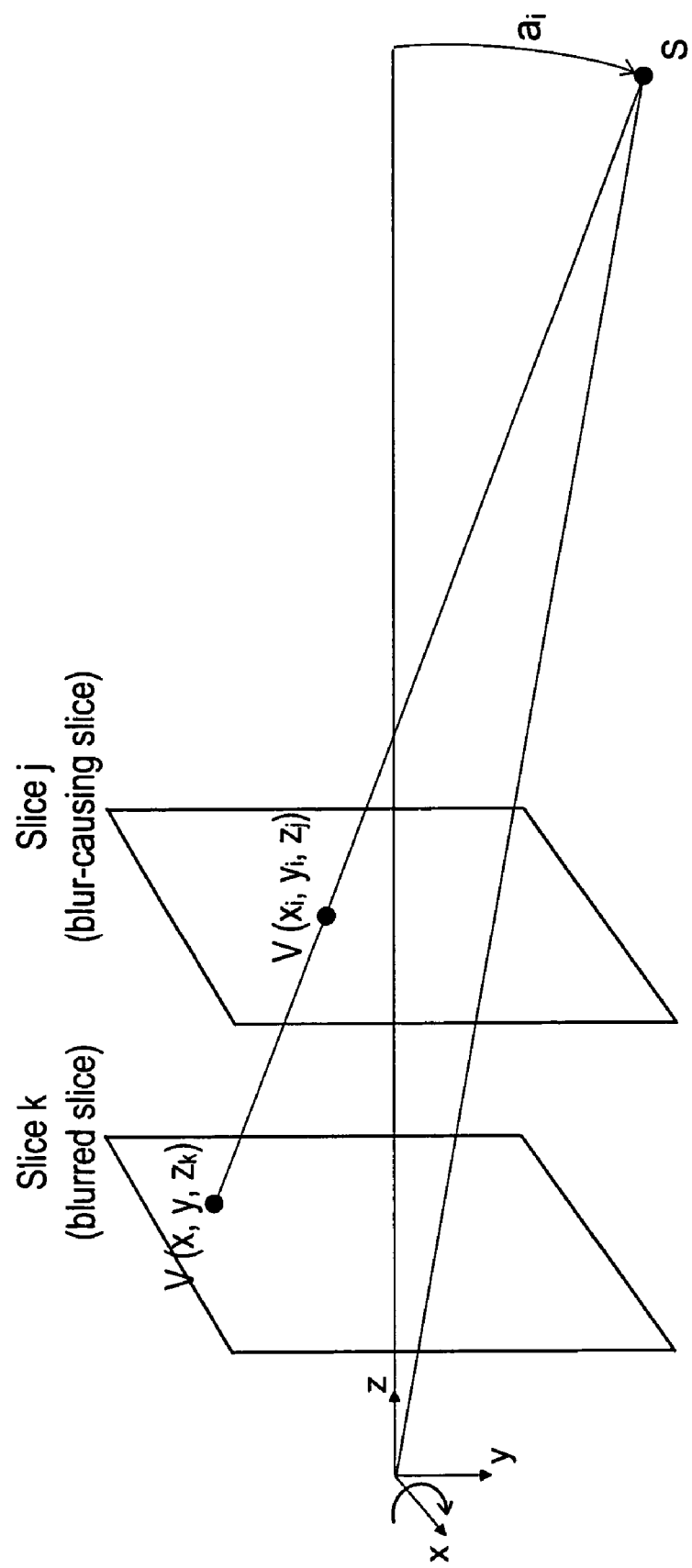

FIG. 5D shows two slices of the set of initially reconstructed tomosynthesis slices 302. Let slice k be the tomosynthesis slice for which one wishes to estimate the blur pattern caused by contrast features outside it. It can be assumed that the initial slice set is large enough, and that it has fine enough spacing, to include most of these contrast features that are enclosed within the volume covered by the source 122 and imager 124 motion. The total contribution to the blur at voxel position (x, y, $z_k$) is given by Equation 4 of FIG. 5B, where $V_b$ is the average of all blur contributions from certain voxels in slices other than slice k. The position of these "blur-causing" voxels in each slice is defined by the X-ray source 122 trajectory relative to the tomosynthesis slices. In Equation 4, while summation over index j represents contribution from different tomosynthesis slices, the summation over index i represents integration of voxel values over a sequence of voxel positions in each tomosynthesis slice. Also in Equation 4, $N_c$ is the averaging count which is normally the number of slices minus one multiplied by the number of input images. Equation 5 gives the deblurred voxel value by subtracting the blur value Vb from the original voxel value. Equations 4 and 5 of FIG. 5B describe the general three-dimensional deblurring process and are not limited to the isocentric geometry. As shown in FIG. 5D, the blur-causing voxel position ($x_i$, $y_i$, $z_j$), corresponding to source 122 position for input image i, is at the intersection of the ray cast from the source 122 for input image i to the voxel position (x, y, $z_k$) on tomosynthesis slice k. For isocentric geometry scenario, this voxel position in slice j is given by Equations 6 and 7 of FIG. 5B. The voxel spacing of the deblurred tomosynthesis slices 330 can be different from the voxel spacing of the initial reconstruction set of tomosynthesis images 302. In some embodiments, it may be advantageous to construct the initial slice set at a finer voxel spacing than the desired final spacing.

It should be noted that the technique for generating the tomosynthesis image(s) is not limited to the examples discussed, and that other known techniques for generating tomosynthesis images can also be used in other embodiments.

In other embodiments, the images (data) used for generating the tomosynthesis images can be a subset of images acquired for a full rotation cone beam CT. For example, while a procedure is being performed to acquire the full cone beam CT set, gated construction of tomosynthesis images (using certain subset(s) of images) can be performed for positioning purposes. In further embodiments, instead of generating the tomosynthesis images 302/330 in step 206, the tomosynthesis images 302/330 are obtained by the processor 54 receiving the tomosynthesis images 302/330 from a device, such as another processor, a computer, or a server.

Figure 4:
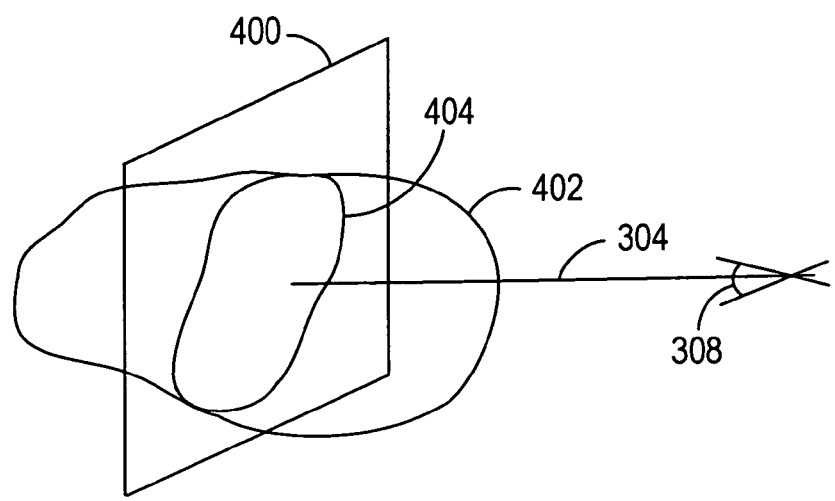
FIG. 4 illustrates a two dimensional image slice being selected from a three dimensional computed tomography image.

Returning to FIG. 2, next, a two-dimensional CT image slice from the reference CT data (obtained from step 202) is obtained, and a tomosynthesis image that best matches the two-dimensional CT image slice is determined (Step 208). In the illustrated embodiments, the two-dimensional CT image slice is determined based on the criteria that (1) it goes through a region of interest (e.g., a treatment region), and (2) it is parallel to the planes of the tomosynthesis images determined from step 206. In some embodiments, the thickness of the CT slice 400 is approximately the same as the depth (in the z-direction) resolution of the tomosynthesis images 302/330, thus making the CT image slice 400 and tomosynthesis images 302/330 more compatible for matching. FIG. 4 illustrates an example in which a two-dimensional CT image slice 400 is selected from the three-dimensional CT image 402, wherein the two-dimensional CT image slice 400 includes a feature (e.g., an image) 404 of target tissue. In the illustrated example, the plane of the two-dimensional CT image slice 400 is parallel to those of the tomosynthesis images 302/330.

After the two-dimensional CT image slice 400 has been determined, the processor 54 then determines a tomosynthesis image 302/330 (e.g., from among the tomosynthesis images 302/330 determined from step 206) that best matches the two-dimensional CT image slice 400. In some embodiments, if the CT image slice 400 and the tomosynthesis image 302/330 have different formats, the processor 54 converts one or both of the respective formats of the CT image slice 400 and the tomosynthesis images 302/330, such that the CT image slice 400 and the tomosynthesis images 302/330 have the same format for comparison. For example, such reformatting may include re-sampling by filtering or interpolation of images. The comparing of the CT image slice 400 and the tomosynthesis images 302/330 can be performed using any imaging techniques known in the art. In some embodiments, a degree of match can be calculated by comparing the two-dimensional CT image slice 400 with each of the tomosynthesis images 302/330. For example, the degree of match can be calculated using a 2D template matching by cross correlating the reference CT slice 400 and the tomosynthesis image 302/330. The degree of match is the value of peak cross correlation. The position of peak cross correlation represents the shift between the reference two-dimensional CT image slice 400 and the tomosynthesis image 302. The matching process is repeated between the reference CT slice 400 and all (or a subset of all) tomosynthesis images 302/330 reconstructed according to a prescribed search range. The tomosynthesis image 302/330 resulting in maximum degree of match and its match position (peak position) is used to localize the target in the three-dimensional space.

Next, the processor 54 then determines a first coordinate (x1, y1, z1) of at least a portion of the target tissue based on matching the two dimensional CT image slice 400 determined in step 202 to one of the tomosynthesis images 302/330 in the search region (Step 210). X1 and y1 are derived from match peak position, and z1 is derived from the position of the matched tomosynthesis slice in the z-direction. In the illustrated embodiments, the offset of the match and the position of the CT image slice 400 provides an initial estimate of the coordinate (e.g., in the treatment system 10 reference) of at least a portion (e.g., a point) of a target tissue. Because the resolution of the tomosynthesis images 302 is higher in their respective x-y planes than in the z-direction, the accuracy of the determined coordinate is relatively higher in the x-direction and y-direction than in the z-direction (i.e., the x1, y1 values are relatively more accurate than the z1 value). However, in some embodiments, if the tomosynthesis images 302 are closely spaced in the z-direction so as to provide sufficient spatial resolution in the z-direction, the initial estimate (x1, y1, z1) of the coordinate can be used as the coordinate of the target tissue.

Figure 6:
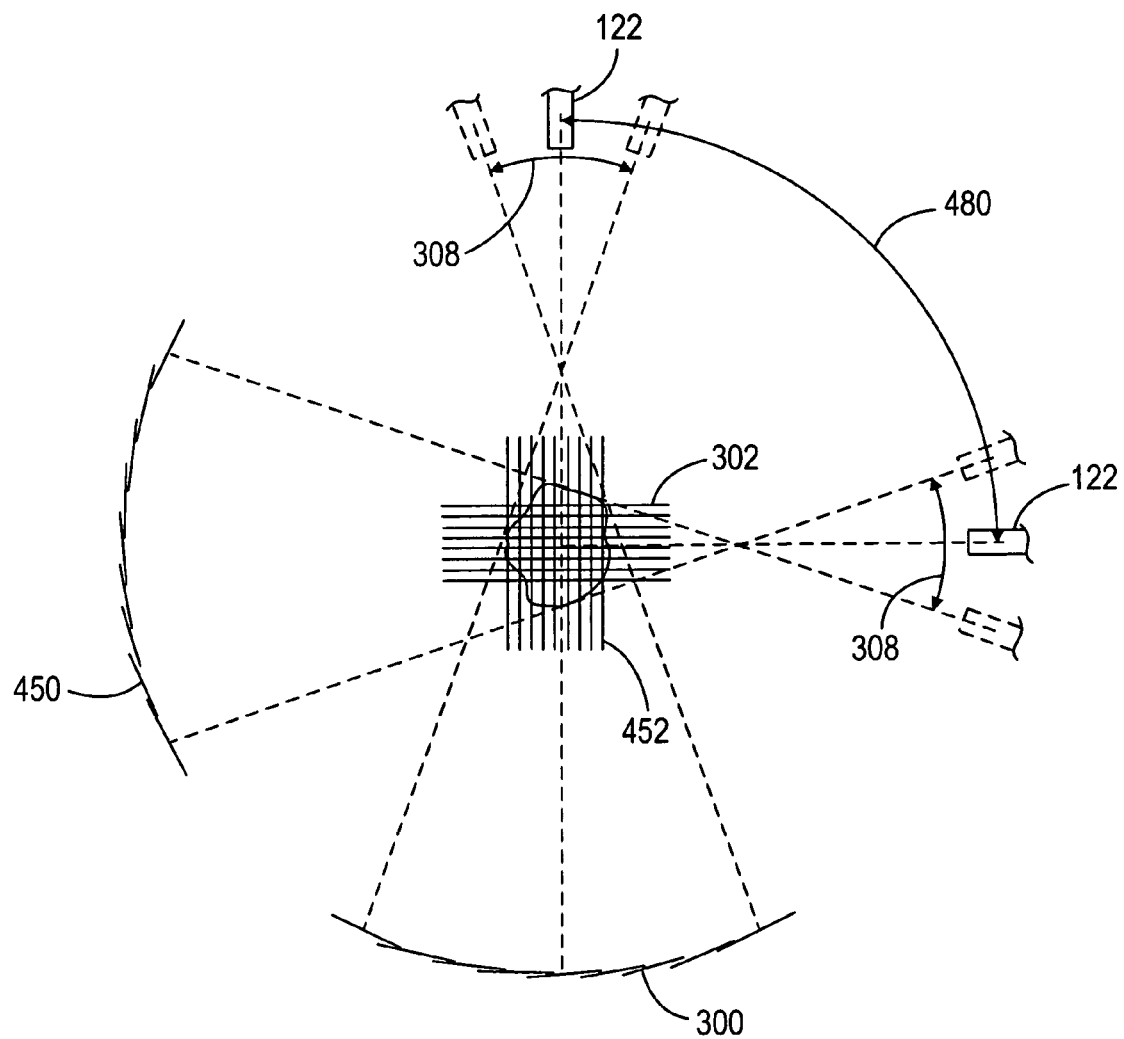
FIG. 6 illustrates two sets of tomosynthesis images being obtained in accordance with some embodiments.

In other embodiments, if additional accuracy for the determined coordinate is desired, the imaging system 120 can be used to obtain a second set of x-ray images, which are then used with the first set of x-ray images 300 to obtain a more accurate coordinate. In particular, the x-ray source 122 and the imager 124 can be positioned to obtain a second set of x-ray images 450, and the x-ray images 450 are then used to construct a second set of tomosynthesis images 452 (FIG. 6). For example, one of the tomosynthesis images 452 can be created such that the first determined coordinate (x1, y1, z1) lies within such tomosynthesis image 452, and the orientation of the second set of tomosynthesis images 452 are at an angle 480 that is approximately 40 to 140 degrees from the orientation of the first set of tomosynthesis images 302. Alternatively, the orientation of the second set of tomosynthesis images 452 can be oriented at other angles relative to the first set of tomosynthesis images 302. Next, the same matching process can be repeated for the slices generated from the second set of images. However this time the reference CT slice 402 while again going through the center of the target volume (as defined in the treatment plan) is normal to the principal axis of the image corresponding to the center of the acquisition arc segment. The above technique can be used to determine a best match with one of the tomosynthesis images 452 (or the enhanced tomosynthesis image if a deblurring technique is used), and a second coordinate (x2, y2, z2) of the target tissue is obtained based on a result of the matching, as similarly discussed previously. In some embodiments, the first coordinate (x1, y1, z1) of the target tissue (obtained from the first set of tomosynthesis images 302) can be used to assist in the determination of the best match for the second set of tomosynthesis images 452. For example, the two best match slices from each set can be viewed as two orthogonal projection views in a stereo viewing geometry. A point (x1, y1) in one view restricts the search for the match point in the other view to a line (called epipolar line). Further determination of the approximate z1 coordinate in the first view restricts the search to a segment of this line. This can assist in reducing the search area for a match in each image with at least one advantage of reducing the probability of producing a false match. Again, because the resolution of the tomosynthesis images 452 is higher in their respective x-y planes than in the z-direction, the accuracy of the second determined coordinate (x2, y2, z2) is relatively higher in the x-direction and y-direction than in the z-direction (i.e., the x2, y2 values are relatively more accurate than the z2 value). In such cases, the (x1, y1) values from the first determined coordinate, and the (x2, y2) values from the second determined coordinate can be used to determine a three dimensional coordinate $(x_t, y_t, z_t)$ of the target tissue using triangulation.

In some embodiments, the three dimensional coordinate $(x_t, y_t, z_t)$ is used as the position of at least a portion (e.g., a point) of a target tissue. Alternatively, if additional accuracy is desired, the above steps 204-210 can be repeated, with the three dimensional coordinate $(x_t, y_t, z_t)$ used to generate the first set of tomosynthesis images 302 such that the coordinate $(x_t, y_t, z_t)$ lies within the plane of one of the tomosynthesis images 302 (Step 212). In other embodiments, if the method 200 does not include generating the second set of tomosynthesis images 452 (i.e., the coordinate $(x_t, y_t, z_t)$ is not available), the first determined three dimensional coordinate (x1, y1, z1) can be used instead, when repeating the steps 204-210, to generate the first set of tomosynthesis images 302 such that the coordinate (x1, y1, z1) lies within the plane of one of the tomosynthesis images 302. The method may be repeated one or more times with the goal of improving the degree of match at each iteration until no additional significant improvement is observed (signifying that the best possible accuracy has been achieved), or until a prescribed number of iteration has been reached.

In some embodiments, the steps 204-210 in method 200 can be performed in a beginning of a treatment session (e.g., before the radiation source 20 is activated to deliver treatment radiation beam to treat the patient 16). For example, the determined three dimensional coordinate of the target tissue in the above method 200 can be used to set up a patient, e.g., to align the patient relative to the radiation treatment system 10, or to align the target tissue relative to the radiation source 20. In other embodiments, the steps 204-210 can be performed during a treatment session (e.g., during a delivery of a treatment radiation beam, or in between deliveries of treatment radiation beam pulses). For example, the determined three dimensional coordinate of the target tissue in the above method 200 can be used to verify a location of the target tissue, to track a movement of the target tissue, and/or to control an operation of the radiation source 20 and/or the collimator 22 (e.g., the processor 504 can be configured to activate or de-activate the radiation source 20, and/or to control position of the leafs in the collimator 22 based on the determined three dimensional coordinate). In such cases, the steps 206-210 are performed in substantially real time (e.g., within seconds after the x-ray images are obtained in step 204).

As illustrated in the above embodiments, because a tomosynthesis image 302 can be generated using relatively few number of x-ray images 300, the tomosynthesis image 302 can be created quickly and without subjecting the patient 16 to extensive radiation (at least when compared to CT imaging). As such, it is more advantageous to use a tomosynthesis image to determine a position of a target tissue than to use a CT image, which requires exposing the patient 16 to more radiation (due to a required quantity of imaging data for CT reconstruction), and much computational resources to generate.

The method 200 of using the system 10 is not limited to the example discussed previously. In other embodiments, one or more steps can be combined with another step in the method 200. In further embodiments, the method 200 needs not include all of the steps 202-210.

Patient Position Sensing System

Figure 7:
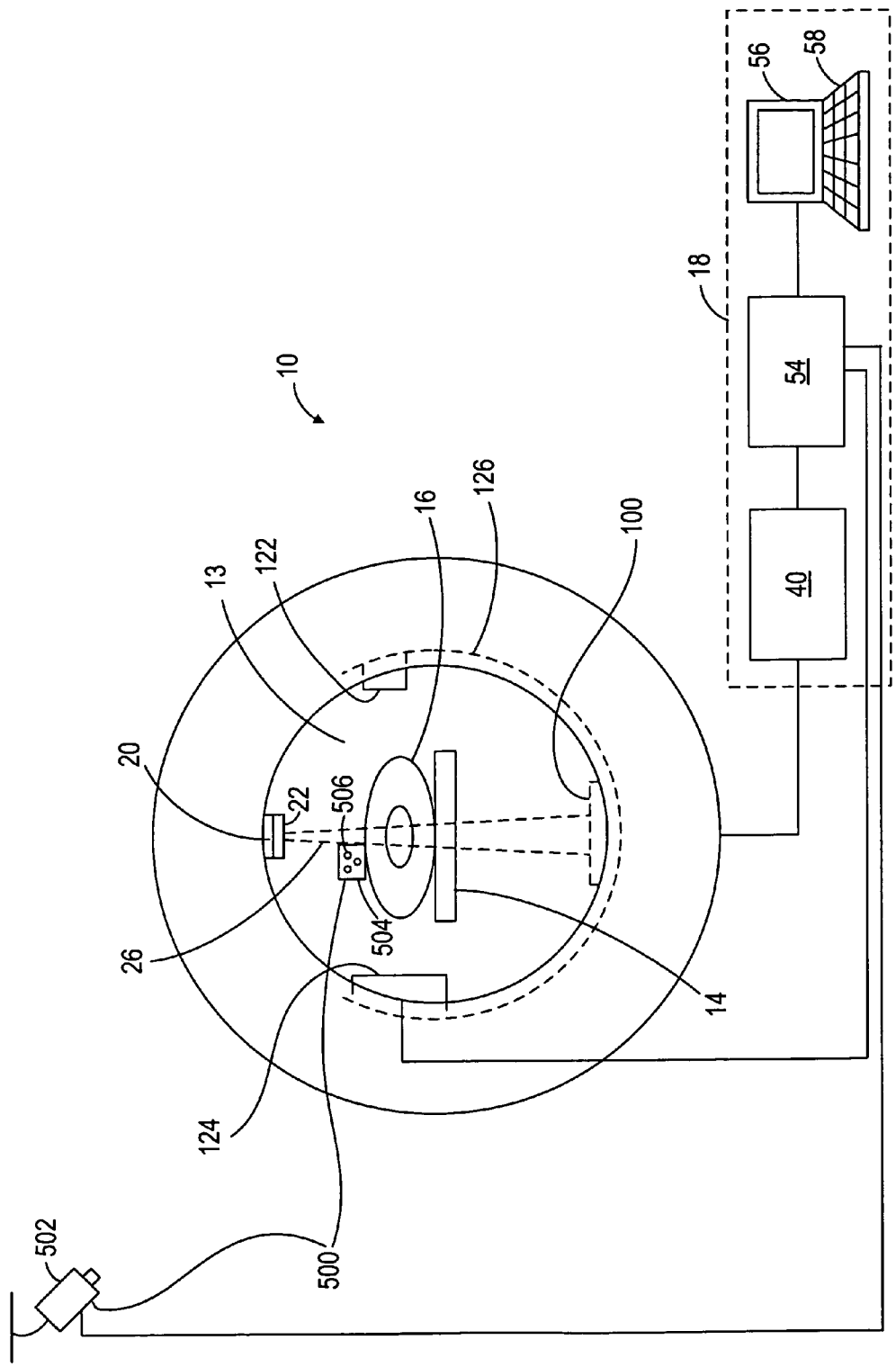
FIG. 7 illustrates the radiation treatment system of FIG. 1, showing the radiation treatment system further having a patient position sensing system in accordance with some embodiments.

In some embodiments, the operation of the radiation treatment system 10 can be based at least in part on a physiological position and/or position of a portion of the patient 16. For example, in any of the embodiments of the radiation treatment system 10 described herein, the system 10 can further include a patient position sensing system 500 (FIG. 7). The patient position sensing system 500 includes an optical device 502 and a marker block 504. In the illustrated embodiments, the optical device 502 is a camera, such as a CCD camera, but can be other type of optical sensor that is capable of sensing an object. The optical device 502 can be mounted to a ceiling, to the system 10, or to a support stand (not shown). The marker block 504 includes a plurality of markers 506 that are so positioned such that at least some of them can be viewed/sensed by the optical device 502. The markers 506 can be implemented using reflective objects. In the illustrated embodiments, the optical device 502 is coupled to the processor 54, which controls an operation of the radiation source 20 and/or the collimator 22 based on input received from the optical device 502.

Alternatively, the optical device 502 can be coupled to a separate processor (not shown) for processing image signals received from the optical device 502.

During use, the marker block 504 is secured to the patient 16, and the optical device 502 is used to sense the positions of at least some of the markers 506 on the marker block 504. Based on the sensed positions of at least some of the markers 506, the processor 54 then determines a position and an orientation of the marker block 504. The determined position and orientation of the marker block 504 can then be used to determine whether the patient 16 has moved and/or an amount of movement undergone by the patient 16.

Although the patient position sensing system 500 has been described as having the optical device 502 and the marker block 504, in other embodiments, other position/movement sensing devices can be used as the patient position sensing system 500. As such, the patient position sensing system 500 may or may not include the optical device 502 and the marker block 504. For example, in other embodiments, the patient position sensing system 500 includes one or more infrared position sensors for sensing at least a part of the patient 16. In other embodiments, the patient position sensing system 500 includes one or more magnetic field sensors, one or more microwave energy sensors, or one or more ultrasound energy sensors, for sensing at least a part of the patient 16.

It should be noted that the patient position sensing system 500 should not be limited by the configuration described previously, and that the patient position sensing system 500 can have other configurations in other embodiments. For example, in other embodiments, instead of a single optical device 502, the patient position sensing system 500 can further include one or more additional optical device(s) 502 for sensing the marker block 504. Also, in other embodiments, the patient position sensing system 500 can further include one or more marker block(s) 504 placed at different location(s) on the patient 16. In further embodiments, instead of having a cube configuration, the marker block 504 can have other shapes, such as a semi-spherical shape, a cone shape, or other customized shapes.

Figure 8:
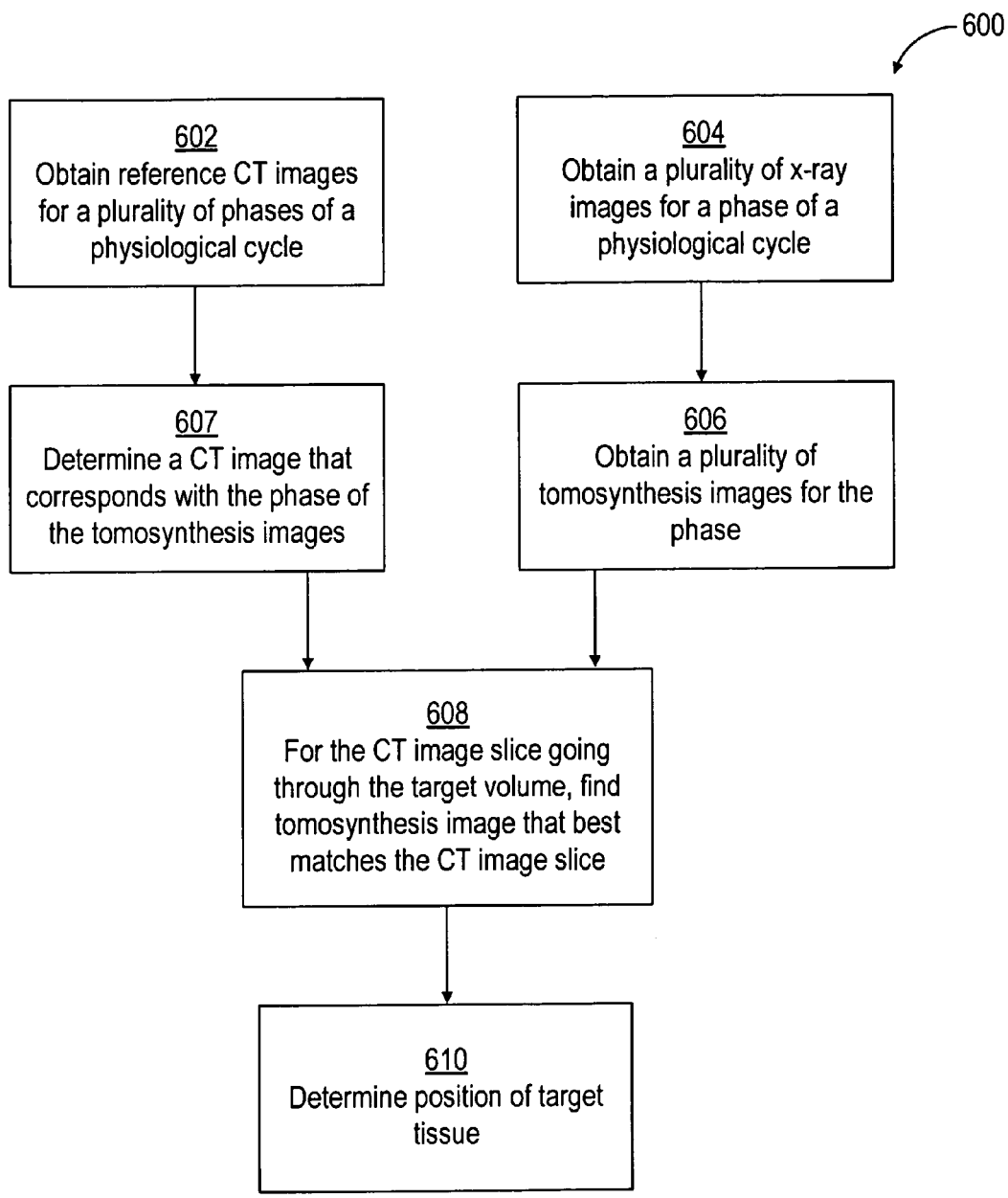
FIG. 8 illustrates a method of determining a position of a target tissue using the tomosynthesis imaging system of FIG. 7 in accordance with some embodiments.

A method 600 of using the imaging system 120 to perform patient registration (e.g., to set up a patient) for the treatment system 10 of FIG. 7 in accordance with some embodiments will now be described with reference to FIG. 8. First, a plurality of computed tomography (CT) images are obtained for a portion of the patient 16 (Step 602). Such can be performed, for example, in a diagnostic session in which the patient 16 is diagnosed, or in a treatment planning session in which a treatment plan is determined. Each of the obtained CT images is generated at a different phase of a physiological cycle of the patient 16, and therefore, is associated with a corresponding phase of a physiological cycle of the patient 16. As used in this specification, the term "phase" refers to a degree of completeness of a physiological cycle (e.g., a breathing cycle or a cardiac cycle) of a portion of a patient. For example, the phase may have a value that is between 0% and 100%. In such cases, a phase value of 50% represents a half-completion of a physiological cycle. As another example, the phase may have a value that is between 0° and 360°. In such cases, a phase value of 180° represents a half-completion of a physiological cycle. In some embodiments, the phase of a physiological cycle can be determined using the patient position sensing system 500. For example, the marker block 504 can be placed on the patient's chest, and the optical device 502 can then be used to sense the position and orientation of the marker block 504 as the patient's chest moves due to the patient's breathing. The marker block positional data (e.g., amplitude data) can then be used to determine a phase of a physiological cycle, as described herein.

Next, during a treatment session, the patient 16 is placed in an operative position associated with the treatment system 10, and the imaging system 120 is used to generate a set of two-dimensional x-ray images 300 (Step 604). The processor 54 then processes the x-ray images 300 to generate a plurality of tomosynthesis images 302 (Step 606). Because the tomosynthesis images 302 are generated using the x-ray images 300 that are obtained during a phase (or a narrow range of phases) of a physiological cycle, the tomosynthesis images 302 are all associated with the same phase of the physiological cycle. Steps 604 and 606 are similar to steps 204 and 206, respectively, of method 200.

Figure 9:
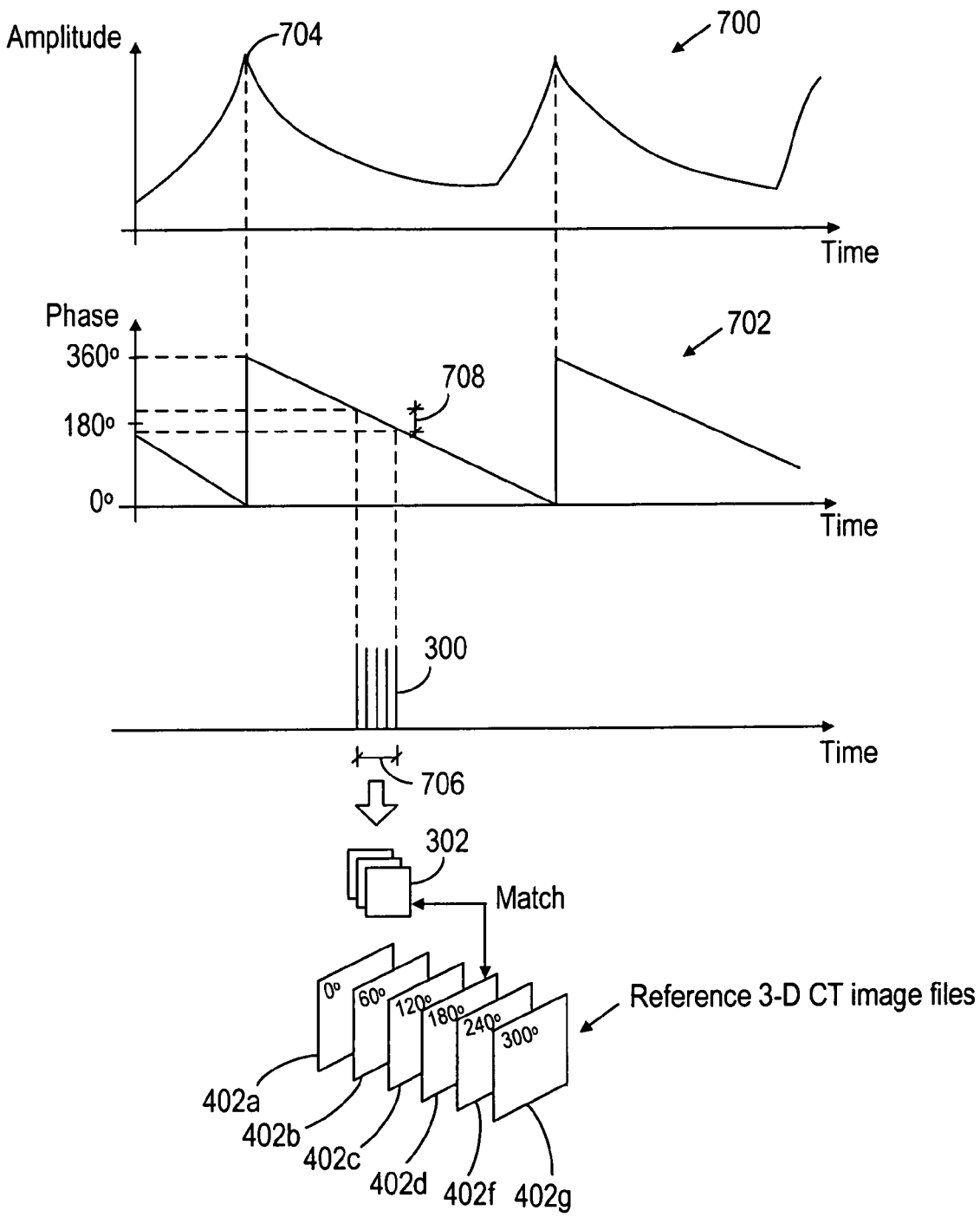
FIG. 9 illustrates a computed tomography image being selected from a plurality of reference computed tomography images.

Next, processor 54 determines a three dimensional CT image from the set of CT images (obtained in step 602) having a phase that corresponds with a phase of the tomosynthesis images 302 (Step 607). Such is illustrated by the diagrams shown in FIG. 9. By monitoring the position of the marker block 504, a diagram 700 showing how an amplitude of a portion (e.g., a chest) of the patient 16 varies over time can be created. Based on the amplitude and time data, a phase diagram 702 can be created, which shows how a degree of completion of a physiological cycle varies over time. In the example, a phase value of 360° or 0° corresponds to a peak 704 of a physiological cycle. FIG. 9 also shows a plurality of x-ray images 300 that are generated (from step 604) within a time period (duration) 706 that corresponds to a phase range 708, and a plurality of tomosynthesis images 302 (generated from step 606). The tomosynthesis images 302 are associated with a phase value (which is 180° in the example) that is the average of the phase range 708. In other embodiments, the x-ray images 300 can be generated at a same phase of a physiological cycle. Such can be accomplished by instructing the patient 16 to perform breath-holds, or to provide multiple x-ray sources and imagers such that a plurality x-ray images can be generated simultaneously. In such cases, the phase value associated with the tomosynthesis images 302 is the phase value at which the x-ray images 300 are generated.

In the example of FIG. 9, the CT images obtained in step 602 include six CT images 402a-402f generated at phase 0° (or 360°), 60°, 120°, 180°, 240°, and 300°, respectively, of a physiological cycle. In step 607, processor 54 selects a CT image from the set of CT images 402, whose phase has the best match with the phase of the tomosynthesis images 302. In the example, since the tomosynthesis images 302 are associated with a phase value of 180°, the processor 54 selects the CT image 402d as the CT image, whose phase (180°) has the best match with the phase of the tomosynthesis images 302. In other embodiments, the matching phase of the tomosynthesis images 302 and the CT image 402 need not be identical. In such cases, the processor 54 selects the CT image 402 whose phase is the closest to the phase of the tomosynthesis images 302. Also, it should be noted that the number of CT images obtained in step 602 is not limited to six as that shown in the example, and that the number of CT images can be more or less than six in other embodiments.

Next, a two-dimensional CT image slice 400 is determined from the CT data set (obtained from step 607), and the processor 54 determines the tomosynthesis image 302 that best matches the two-dimensional CT image slice 400 (Step 608). As similarly discussed, in some embodiments, the two-dimensional CT image slice 400 can be selected based on the criteria that (1) it goes through a region of interest (e.g., a treatment region), and (2) it is parallel to the planes of the tomosynthesis images determined from step 606. After the two dimensional CT image slice 400 has been determined, and a tomosynthesis image that matches with the CT image slice 400 has been determined, the processor 54 then determines a first coordinate (x1, y1, z1) of the target tissue based data obtained from the matching (Step 610). Steps 608 and 610 are similar to steps 208 and 210, respectively, of method 200. In some embodiments, the first coordinate (x1, y1, z1) is used as the coordinate of the target tissue. In other embodiments, a second set of tomosynthesis images 452 can be generated to obtain a second coordinate (x2, y2, z2), and the (x1, y1) values from the first coordinate, and the (x2, y2) values from the second coordinate are then used to calculate a three dimensional coordinate $(x_t, y_t, z_t)$ for the target tissue using triangulation, as discussed previously. In some embodiments, the second set of input images can be acquired while breathing is in the same phase, and the gantry is at sufficiently different angle, e.g., greater than 40°, from that associated with the first set.

In some embodiments, the above described process can be repeated for a different phase of a physiological cycle. For example, the above process can be repeated for N times, where the value N corresponds to the number of CT images 402 obtained in step 602.

The result obtained from the above described process can be used for a variety of purposes. In some embodiments, the result can be used for verification of the gating thresholds (e.g., to verify whether a target is in the planned location as defined by a reference image during or outside a gated interval as sensed, for example, by the above position sensing system 500). In other embodiments, the result can also be used for continuous tracking of a target that moves, e.g., due to breathing. In further embodiments, the patient position sensing device described can also be used to estimate breathing motion and its phase for the gated setup application.

Figure 10:
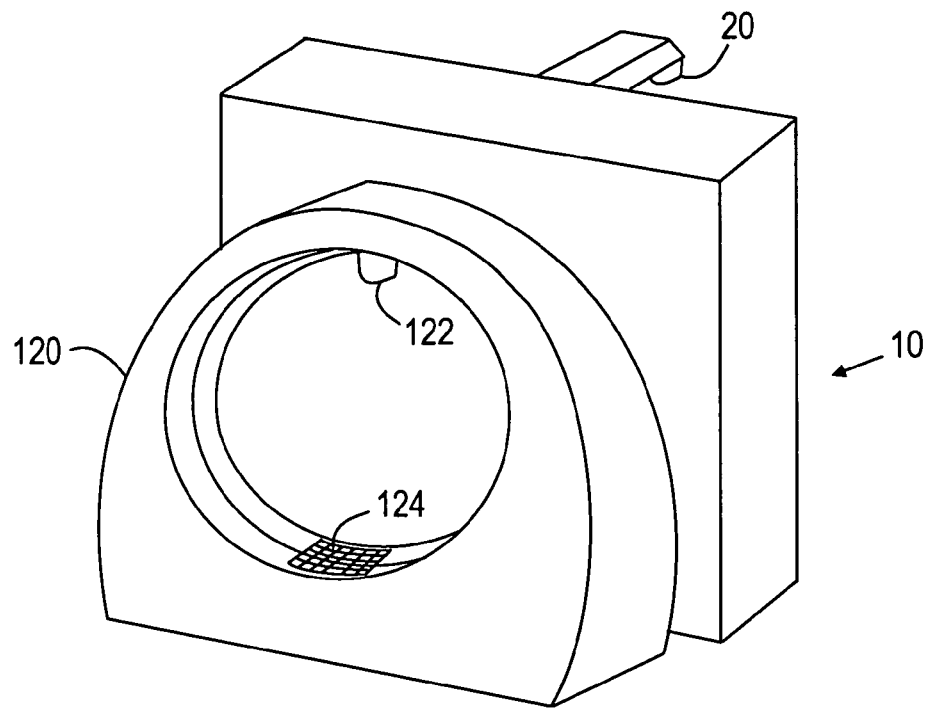
FIG. 10 illustrates a radiation treatment system having a tomosynthesis imaging system in accordance with other embodiments.
Figure 11:
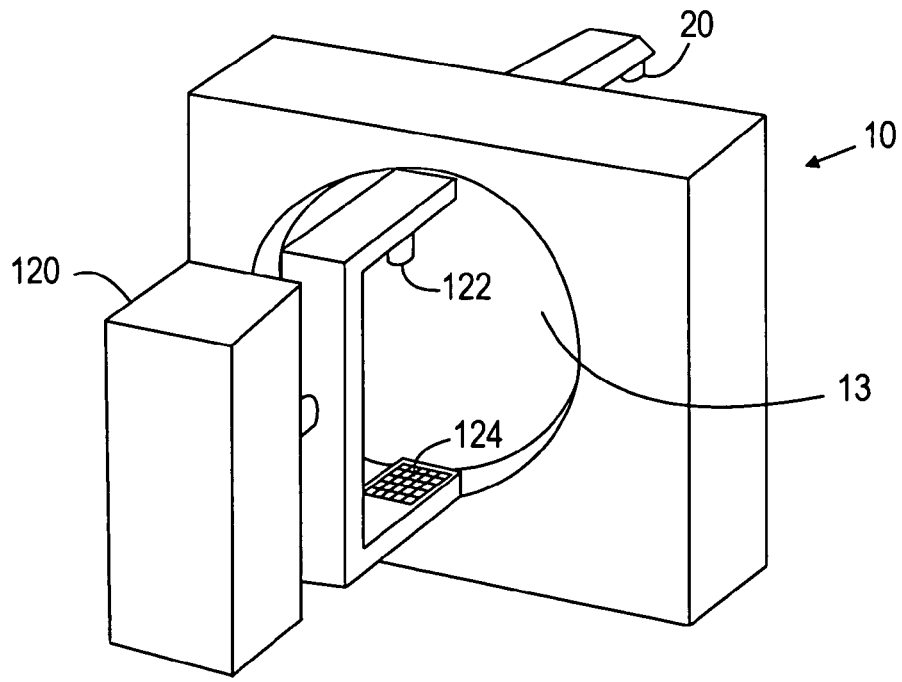
FIG. 11 illustrates a radiation treatment system having a tomosynthesis imaging system in accordance with other embodiments.

It should be noted that the tomosynthesis imaging system 120 is not limited to the example described previously, and that the tomosynthesis imaging system 120 can have other configurations in other embodiments. For example, in other embodiments, the tomosynthesis imaging system 120 is implemented as a separate device from a treatment machine (FIG. 10). In other embodiments, the tomosynthesis imaging system 120 can have a C-arm configuration (FIG. 11). In further embodiments, the x-ray source 122 and imager 124 of the tomosynthesis imaging system 120 do not move in a circular (or partial circular) motion. For example, the x-ray source 122 can be configured to move in a translational motion. In other embodiments, the source 122 is configured to move in a plane that is parallel to the imager plane. Other types of source-imager relative motion may also be used in other embodiments.

Further, in other embodiments, the system 10 does not include the imaging system 120. In such cases, instead of generating tomosynthesis image(s) using the imaging system 120, the radiation source 20 and the imager 100 can be used to generate data for reconstruction of the tomosynthesis image (s). During a treatment procedure, the radiation source 20 can alternately deliver treatment radiation for treating targeted tissue, and diagnostic radiation for generating data that can be used to determine tomosynthesis image(s).

In addition, although the above system 10 and methods 200, 600 have been described with reference to obtaining CT image data as reference image(s), in other embodiments, instead of CT image(s), other forms of image can be used. For example, in other embodiments, instead of obtaining CT image(s) in step 202, the processor 54 of the system 10 receives tomosynthesis images, fluoroscopic image(s), PET image(s), ultrasound image(s), MRI image(s), or SPECT image(s), for use as reference images.

Further, in other embodiments, instead of a treatment radiation system, the system 10 can be any of a variety of machines, such as a diagnostic machine, a simulator, a inspection machine, or another machine (e.g., an On-Board-Imaging (OBI) machine) that may or may not be configured to deliver radiation. For example, in some embodiments, the system 10 can include a robotic arm for performing an operation on a patient. In such cases, the imaging system 120 can be used to set up the patient relative to the robotic arm. Also, in other embodiments, the system 10 may not be a machine for medical use.

Computer System Architecture

Figure 12:
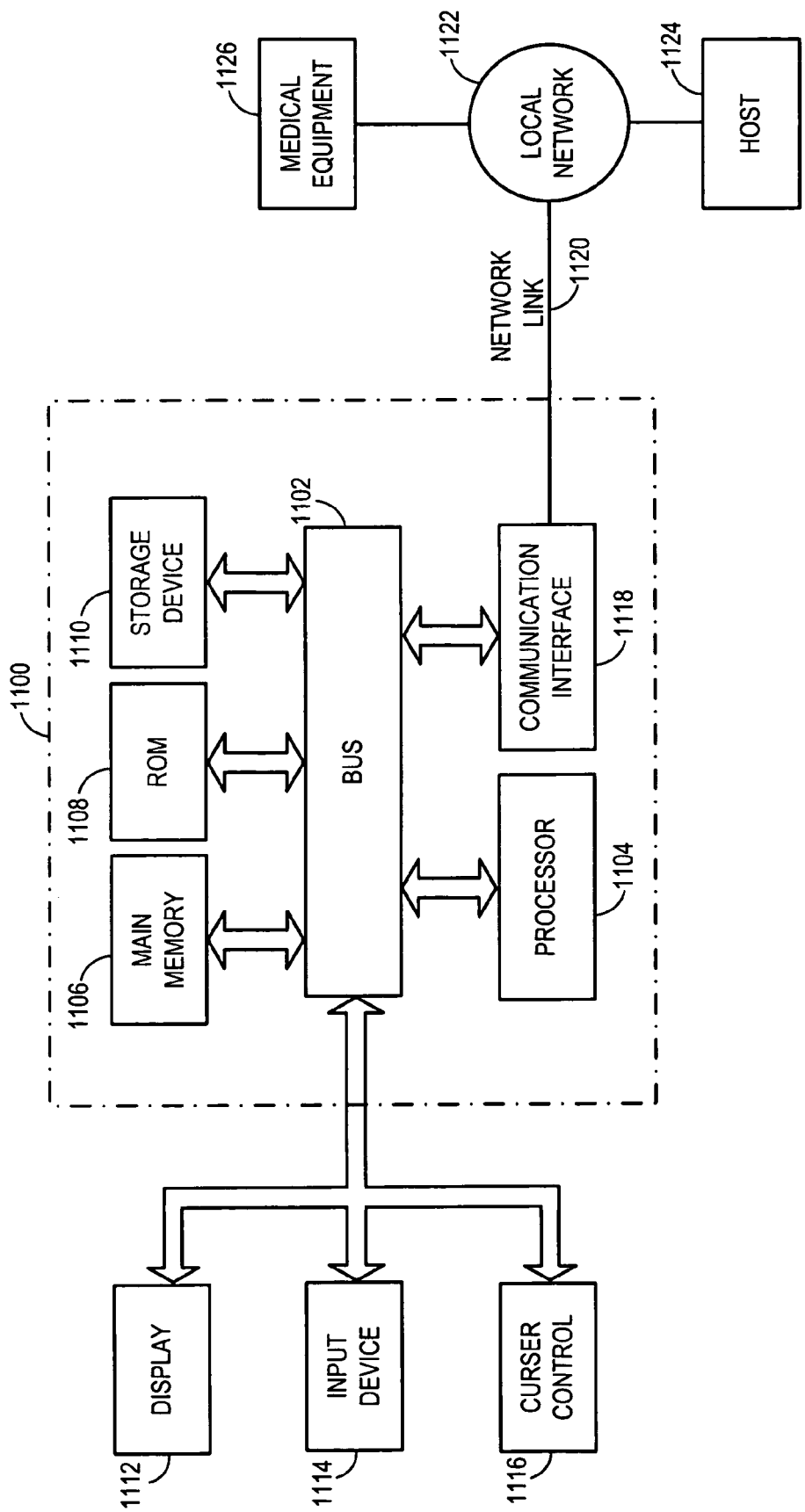
FIG. 12 illustrates a block diagram of a computer system that can be used to perform various functions described herein in accordance with some embodiments.

FIG. 12 is a block diagram illustrating an embodiment of a computer system 1100 that can be used to perform various functions described herein. Computer system 1100 includes a bus 1102 or other communication mechanism for communicating information, and a processor 1104 coupled with the bus 1102 for processing information. The processor 1104 may be an example of the processor 54, or alternatively, an example of a component of the processor 54, of FIG. 1. The computer system 1100 also includes a main memory 1106, such as a random access memory (RAM) or other dynamic storage device, coupled to the bus 1102 for storing information and instructions to be executed by the processor 1104. The main memory 1106 also may be used for storing temporary variables or other intermediate information during execution of instructions to be executed by the processor 1104. The computer system 1100 further includes a read only, memory (ROM) 1108 or other static storage device coupled to the bus 1102 for storing static information and instructions for the processor 1104. A data storage device 1110, such as a magnetic disk or optical disk, is provided and coupled to the bus 1102 for storing information and instructions.

The computer system 1100 may be coupled via the bus 1102 to a display 117, such as a cathode ray tube (CRT), for displaying information to a user. An input device 1114, including alphanumeric and other keys, is coupled to the bus 1102 for communicating information and command selections to processor 1104. Another type of user input device is cursor control 1116, such as a mouse, a trackball, or cursor direction keys for communicating direction information and command selections to processor 1104 and for controlling cursor movement on display 117. This input device typically has two degrees of freedom in two axes, a first axis (e.g., x) and a second axis (e.g., y), that allows the device to specify positions in a plane.

In some embodiments, the computer system 1100 can be used to perform various functions described herein. According to some embodiments of the invention, such use is provided by computer system 1100 in response to processor 1104 executing one or more sequences of one or more instructions contained in the main memory 1106. Those skilled in the art will know how to prepare such instructions based on the functions and methods described herein. Such instructions may be read into the main memory 1106 from another computer-readable medium, such as storage device 1110. Execution of the sequences of instructions contained in the main memory 1106 causes the processor 1104 to perform the process steps described herein. One or more processors in a multi-processing arrangement may also be employed to execute the sequences of instructions contained in the main memory 1106. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 1104 for execution. Such a medium may take many forms, including but not limited to, non-volatile media, volatile media, and transmission media. Non-volatile media includes, for example, optical or magnetic disks, such as the storage device 1110. Volatile media includes dynamic memory, such as the main memory 1106. Transmission media includes coaxial cables, copper wire and fiber optics, including the wires that comprise the bus 1102. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1104 for execution. For example, the instructions may initially be carried on a magnetic disk of a remote computer. The remote computer can load the instructions into its dynamic memory and send the instructions over a telephone line using a modem. A modem local to the computer system 1100 can receive the data on the telephone line and use an infrared transmitter to convert the data to an infrared signal. An infrared detector coupled to the bus 1102 can receive the data carried in the infrared signal and place the data on the bus 1102. The bus 1102 carries the data to the main memory 1106, from which the processor 1104 retrieves and executes the instructions. The instructions received by the main memory 1106 may optionally be stored on the storage device 1110 either before or after execution by the processor 1104.

The computer system 1100 also includes a communication interface 1118 coupled to the bus 1102. The communication interface 1118 provides a two-way data communication coupling to a network link 1120 that is connected to a local network 1122. For example, the communication interface 1118 may be an integrated services digital network (ISDN) card or a modem to provide a data communication connection to a corresponding type of telephone line. As another example, the communication interface 1118 may be a local area network (LAN) card to provide a data communication connection to a compatible LAN. Wireless links may also be implemented. In any such implementation, the communication interface 1118 sends and receives electrical, electromagnetic or optical signals that carry data streams representing various types of information.

The network link 1120 typically provides data communication through one or more networks to other devices. For example, the network link 1120 may provide a connection through local network 1122 to a host computer 1124 or to equipment 1126, such as any of the devices herein (e.g., device 166, system 10, patient support system 200, etc.), or a switch operatively coupled to any of the devices described herein. The data streams transported over the network link 1120 can comprise electrical, electromagnetic or optical signals. The signals through the various networks and the signals on the network link 1120 and through the communication interface 1118, which carry data to and from the computer system 1100, are exemplary forms of carrier waves transporting the information. The computer system 1100 can send messages and receive data, including program code, through the network(s), the network link 1120, and the communication interface 1118.

Although particular embodiments have been shown and described, it will be understood that it is not intended to limit the claimed inventions, and it will be obvious to those skilled in the art that various changes and modifications may be made without departing from the spirit and scope of the application. For example, in other embodiments, the radiation treatment system 10 or the imaging system 120 may not include one or more of the components described herein. Also, the operations performed by the processor 54 can be performed by any combination of hardware and software, and should not be limited to particular embodiments comprising a particular definition of "processor." In addition, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A system for processing images, comprising:
an imaging system having a x-ray source and an imager; and
a processor configured to
obtain a tomosynthesis image of an object for a phase of a first physiological cycle of a patient during a first time period using the imaging system, receive a plurality of reference computed tomography (CT) images that are generated at respective phases of a second physiological cycle of the patient during a second time period, select a CT image from the plurality of reference CT images, wherein the selected CT image has a corresponding phase that best matches with the phase associated with the tomosynthesis image, compare the tomosynthesis image with a subset of the CT image, and determine a position of the object based at least in part on a result of the comparison.

2. The system of claim 1, wherein the imager is configured to rotate over an angle that is between 5° and 45° to obtain a number of x-ray images.

3. The system of claim 1, wherein the source is configured to generate a number of x-ray images, wherein the number is a value that is between 5 and 100.

4. The system of claim 1, further comprising a treatment radiation source, wherein the position of the object is determined relative to a coordinate system associated with the treatment radiation source.

5. The system of claim 1, wherein the processor is further configured to perform a deblurring procedure to modify the tomosynthesis image.

6. The system of claim 1, wherein the subset of the CT image comprises a two dimensional CT image slice of the CT image.

7. The system of claim 1, wherein the processor is further configured to compare another tomosynthesis image with the subset of the CT image.

8. A method of determining a position of an object, at least part of the method implemented using a processor, the method comprising:

obtaining an image of an object, wherein the image comprises a tomosynthesis image, wherein the object comprises a part of a patient, and the image is obtained for a phase of a first physiological cycle of the patient during a first time period;

receiving a plurality of reference computed tomography (CT) images that are generated at respective phases of a second physiological cycle of the patient during a second time period;

selecting one of the plurality of reference CT images having a corresponding phase that best matches the phase of the image;

obtaining a reference image of the object, the reference image having a plane that is parallel with a plane of the image, wherein the reference image comprises a subset of the selected one of the plurality of reference CT images;

comparing the reference image with the image; and determining a coordinate of the object based at least in part on a result of the comparing.

9. The method of claim 8, wherein the obtaining the image comprises:

obtaining a first x-ray image of the object using a x-ray source that is located at a first position;

moving the x-ray source from the first position to a second position;

obtaining a second x-ray image of the object using the x-ray source at the second position; and processing the first and the second x-ray images.

10. The method of claim 9, wherein the first and the second x-ray images are processed to obtain a set of digital tomosynthesis images.

11. The method of claim 10, wherein the obtaining the image further comprises selecting one of the digital tomosynthesis images as the image, and the method further comprises:

comparing another one of the digital tomosynthesis images with the reference image;

wherein the coordinate is determined based at least in part on a result of one of the comparing that indicates a better match.

12. The method of claim 10, wherein the obtaining the image further comprises deblurring one or more of the digital tomosynthesis images.

13. The method of claim 8, wherein the selected one of the plurality of reference CT images is a three-dimensional image, and wherein the reference image comprises a two-dimensional image determined from the selected one of the plurality of reference CT images.

14. The method of claim 8, wherein the coordinate of the object is expressed with reference to a coordinate system of a radiation machine.

15. The method of claim 14, wherein the radiation machine is selected from the group consisting of a treatment machine, a diagnostic machine, a simulator, an inspection machine, and a machine that is capable of performing a treatment procedure and a diagnostic procedure.

16. A method of determining a position of an object, at least part of the method implemented using a processor, the method comprising:

obtaining a tomosynthesis image of an object, wherein the object comprises a patient, the tomosynthesis image is obtained for a phase of a first physiological cycle of the patient during a first time period;

receiving a plurality of three-dimensional reference computed tomography (CT) images that are generated at respective phases of a second physiological cycle of the patient during a second time period;

selecting one of the plurality of three-dimensional reference CT images having a corresponding phase that best matches the phase of the tomosynthesis image;

determining a two dimensional CT image from the selected one of the plurality of three-dimensional reference CT images;

determining a match between the tomosynthesis image and a two-dimensional CT image that is a subset of the three-dimensional CT image; and determining a coordinate of the object relative to a radiation machine based at least in part on the determined match.

17. The method of claim 16, further comprising comparing another tomosynthesis image with the two-dimensional CT image.

18. The method of claim 16, wherein the obtaining the tomosynthesis image comprises:

obtaining a first x-ray image of the object using a x-ray source that is located at a first position;

moving the x-ray source from the first position to a second position;

obtaining a second x-ray image of the object using the x-ray source at the second position; and processing the first and the second x-ray images.

19. The method of claim 18, wherein the first and the second x-ray images are processed to obtain a set of digital tomosynthesis images.

20. The method of claim 19, wherein the obtaining the tomosynthesis image further comprises selecting one of the digital tomosynthesis images as the tomosynthesis image, and the method further comprises:

comparing another one of the digital tomosynthesis images with the two-dimensional CT image to determine another match;
wherein the coordinate is determined based at least in part on one of the matches that indicates a better match.

21. The method of claim 19, further comprising deblurring one or more of the digital tomosynthesis images.

22. The method of claim 16, wherein the two dimensional CT image has an orientation relative to the object that corresponds with an orientation of the tomosynthesis image.

23. The method of claim 16, wherein the determining the coordinate comprises comparing the two dimensional CT image with the tomosynthesis image.

24. The method of claim 16, wherein the radiation machine is selected from the group consisting of a treatment machine, a diagnostic machine, a simulator, and a machine that is capable of performing a treatment procedure and a diagnostic procedure.

25. The method of claim 16,
wherein the tomosynthesis image is obtained by receiving a plurality of x-ray images and processing the x-ray images using a back projection technique.

26. The method of claim 25, wherein the tomosynthesis image is obtained by performing a filtering procedure.

27. The method of claim 26, wherein the filtering procedure is performed after the back projection procedure is performed.

28. The method of claim 25, wherein the number of x-ray images is less than that associated with a complete set for forming a volumetric CT image.

29. A method for use in a radiation treatment procedure, at least part of the method implemented using a processor, the method comprising:
obtaining a first tomosynthesis image of an object;
determining a first two dimensional coordinate of the object using the first tomosynthesis image;
obtaining a second tomosynthesis image of the object;
determining a second two dimensional coordinate of the object using the second tomosynthesis image; and
determining a three dimensional coordinate of the object using a processor based on the first and second two dimensional coordinates, wherein the act of determining the three dimensional coordinate is performed during a radiation treatment section;
wherein the act of determining the three dimensional coordinate based at least in part on the first and the second two dimensional coordinates is performed during a delivery of a treatment radiation beam or between deliveries of treatment radiation beam pulses to treat a target at an isocenter.

30. The method of claim 29, wherein the obtaining the first tomosynthesis image comprises:
obtaining a first x-ray image of the object using a x-ray source that is located at a first position;
moving the x-ray source from the first position to a second position;
obtaining a second x-ray image of the object using the x-ray source at the second position; and
processing the first and the second x-ray images.

31. The method of claim 30, wherein the first and the second x-ray images are processed to obtain a set of digital tomosynthesis images.

32. The method of claim 31, wherein the obtaining the first tomosynthesis image further comprises selecting one of the digital tomosynthesis images as the first tomosynthesis image.

33. The method of claim 31, further comprising deblurring one or more of the digital tomosynthesis images.

34. The method of claim 29, wherein the determining the three dimensional coordinate of the object comprises performing a triangulation procedure using the first and the second two dimensional coordinates.

35. The method of claim 29, further comprising controlling a treatment radiation source or a collimator based at least in part on the three dimensional coordinate that is determined using the first and the second tomosynthesis images respectively.

36. The method of claim 29, further comprising tracking a movement of the object during the radiation treatment session based at least in part on the three dimensional coordinate.

37. A device for use in a radiation treatment procedure, comprising:
a processor configured for:
obtaining a first tomosynthesis image of an object,
determining a first two dimensional coordinate of the object using the first tomosynthesis image,
obtaining a second tomosynthesis image of the object,
determining a second two dimensional coordinate of the object using the second tomosynthesis image, and
determining a three dimensional coordinate of the object during a radiation treatment session based at least in part on the first and the second two dimensional coordinates; and
a memory for storing the first and second tomosynthesis images;
wherein the processor is configured to determine the three dimensional coordinate during a delivery of a treatment radiation beam or between deliveries of treatment radiation beam pulses to treat a target at an isocenter.

38. The device of claim 37, wherein the processor is configured to control a treatment radiation source or a collimator based at least in part on the three dimensional coordinate that is determined using the first and the second tomosynthesis images respectively.

39. The device of claim 37, wherein the processor is configured to track a movement of the object during the radiation treatment session based at least in part on the three dimensional coordinate.

* * * * *